US012161870B2

(12) United States Patent
Zhang et al.

(10) Patent No.: US 12,161,870 B2
(45) Date of Patent: *Dec. 10, 2024

(54) FITTING ALGORITHM FOR RECRUITING OF NEURAL TARGETS IN A SPINAL CORD STIMULATOR SYSTEM

(71) Applicant: Boston Scientific Neuromodulation Corporation, Valencia, CA (US)

(72) Inventors: Tianhe Zhang, Studio City, CA (US); Que Doan, West Hills, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 258 days.

This patent is subject to a terminal disclaimer.

(21) Appl. No.: 17/808,459

(22) Filed: Jun. 23, 2022

(65) Prior Publication Data

US 2022/0323758 A1  Oct. 13, 2022

Related U.S. Application Data

(63) Continuation of application No. 16/737,663, filed on Jan. 8, 2020, now Pat. No. 11,413,457.

(60) Provisional application No. 62/795,268, filed on Jan. 22, 2019.

(51) Int. Cl.
| | | |
|---|---|---|
| *A61N 1/36* | (2006.01) | |
| *A61N 1/372* | (2006.01) | |
| *G16H 20/30* | (2018.01) | |
| *G16H 40/67* | (2018.01) | |

(52) U.S. Cl.
CPC ..... *A61N 1/36071* (2013.01); *A61N 1/36132* (2013.01); *A61N 1/36139* (2013.01); *A61N 1/37217* (2013.01); *A61N 1/37247* (2013.01); *G16H 20/30* (2018.01); *G16H 40/67* (2018.01)

(58) Field of Classification Search
CPC ............ A61N 1/36071; A61N 1/36132; A61N 1/36139; G16H 20/30; G16H 40/67
USPC .......................................................... 607/46
See application file for complete search history.

(56) References Cited

U.S. PATENT DOCUMENTS

| | | |
|---|---|---|
| 6,181,969 B1 | 1/2001 | Gord |
| 6,516,227 B1 | 2/2003 | Meadows et al. |
| 7,024,247 B2 | 4/2006 | Gliner et al. |
| 7,424,322 B2 | 9/2008 | Lombardi et al. |
| 7,450,992 B1 | 11/2008 | Cameron |
| 8,255,057 B2 | 8/2012 | Fang et al. |

(Continued)

*Primary Examiner* — Nadia A Mahmood
(74) *Attorney, Agent, or Firm* — Lewis & Reese, PLLC

(57) ABSTRACT

A fitting algorithm for a spinal cord stimulator is disclosed, which is preferably implemented in a clinician programmer having a graphical user interface. In one example, coupling parameters indicative of coupling to neural structures are determined for each electrode in an implanted electrode array. The user interface associates different pole configurations with different anatomical targets and with different measurement techniques (subjective or objective) to gauge the effectiveness of the pole configuration at different positions in the electrode array. The pole configuration, perhaps as modified by the coupling parameters, is then steered in the array, and effectiveness is measured along with a paresthesia threshold at each position. Using at least this data, the fitting algorithm can determine one or more candidate positions in the electrode array at which a therapeutic stimulation program can be centered.

20 Claims, 17 Drawing Sheets

(56) References Cited

U.S. PATENT DOCUMENTS

| | | |
|---|---|---|
| 8,335,664 B2 | 12/2012 | Eberle |
| 8,606,362 B2 | 12/2013 | He et al. |
| 8,620,436 B2 | 12/2013 | Parramon et al. |
| 9,044,155 B2 | 6/2015 | Strahl |
| 9,248,274 B2 | 2/2016 | Troosters et al. |
| 9,248,279 B2 | 2/2016 | Chen et al. |
| 9,302,112 B2 | 4/2016 | Bornzin et al. |
| 9,403,013 B2 | 8/2016 | Walker et al. |
| 9,409,020 B2 | 8/2016 | Parker |
| 9,526,897 B2 | 12/2016 | Chen et al. |
| 9,731,116 B2 | 8/2017 | Chen |
| 10,076,667 B2 | 9/2018 | Kaula et al. |
| 2012/0092031 A1 | 4/2012 | Shi et al. |
| 2012/0095519 A1 | 4/2012 | Parramon et al. |
| 2012/0095529 A1 | 4/2012 | Parramon et al. |
| 2015/0157861 A1 | 6/2015 | Aghassian |
| 2015/0231402 A1 | 8/2015 | Aghassian |
| 2015/0360038 A1 | 12/2015 | Zottola et al. |
| 2017/0182322 A1 | 6/2017 | Grill et al. |
| 2018/0071513 A1 | 3/2018 | Weiss et al. |
| 2018/0071516 A1 | 3/2018 | Weiss et al. |
| 2018/0071520 A1 | 3/2018 | Weerakoon et al. |
| 2018/0071527 A1 | 3/2018 | Feldman et al. |
| 2018/0140831 A1 | 5/2018 | Feldman et al. |
| 2018/0214689 A1* | 8/2018 | Zhang ................ A61N 1/36185 |
| 2019/0009094 A1 | 1/2019 | Zhang et al. |
| 2019/0046800 A1 | 2/2019 | Doan et al. |
| 2019/0083796 A1 | 3/2019 | Weerakoon et al. |
| 2019/0099602 A1 | 4/2019 | Esteller et al. |
| 2019/0366104 A1 | 12/2019 | Doan et al. |
| 2020/0001091 A1 | 1/2020 | Marnfeldt et al. |
| 2020/0061380 A1 | 2/2020 | Zhang et al. |

* cited by examiner

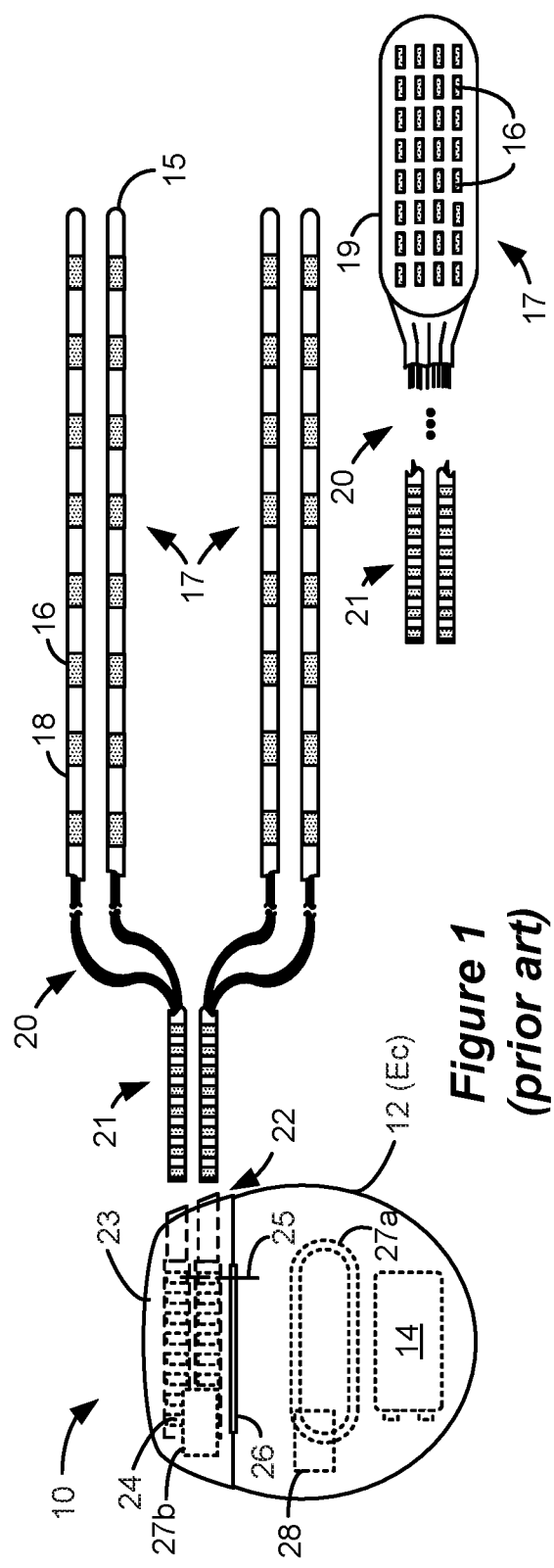
*Figure 1 (prior art)*
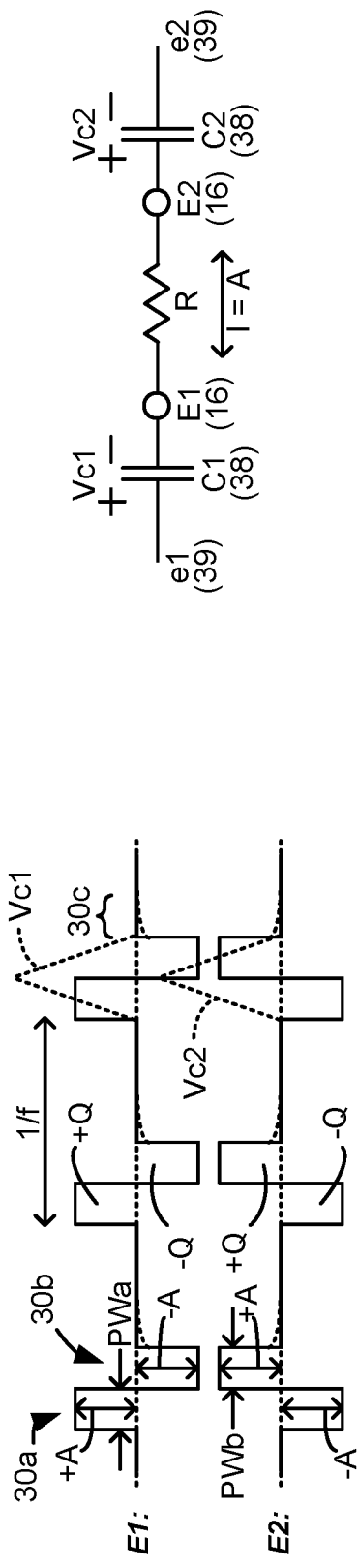
*Figure 2B (prior art)*
*Figure 2A (prior art)*

Select anatomical target/pole configuration for search 106

| Select | Anatomical target | Searching pole configuration | | Measurement aspects | | | Default therapeutic stimulation program |
|---|---|---|---|---|---|---|---|
| | | Pole Definition | Current fraction and position of each pole | Measured neural response | Measure-ment | Patient measurement (M) metrics | |
| 1 | Dorsal column | tripole | +50(-2),-100(0),+50(+2) | Traditional Paresthesia | subjective | patient | SP1 |
| 2 | Dorsal column | tripole | +50(-2),-100(0),+50(+2) | ECAPs | objective | +5,+6,-4 | SP2 |
| 3 | Dorsal roots | Spread monopole | -36(-2),-4(-1),-20(0), -4(+1),-36(+2) | Anatomical Paresthesia | subjective | patient | SP3 |
| 4 | Dorsal roots | Spread monopole | -36(-2),-4(-1),-20(0), -4(+1),-36(+2) | Proprioception | subjective | patient | SP4 |
| 5 | Dorsal roots | Spread bipole | -36(-6),-4(-3),-20(0), -4(+3),-36(+6) | DRPs | objective | (+1,+2),(+4,+5), (+7,+8) | SP5 |
| 6 | Net effect | Spread bipole | +67(-2),+33(-1), -33(+1),-67(+2) | EEG | objective | Scalp | SP6 |
| 7 | Dorsal horn/ ventral roots | Bipole | -100(0),+100(+1) | EMG | objective | R leg, L leg | SP7 |

GUI 120

131

% of anodic (+) or cathodic (-) current

Position of pole in configuration:
0 = center
+ = rostral
- = caudal

*Figure 9*

*Anatomical paresthesia (dorsal roots):*

*ECAPs (dorsal column):*

FITTING ALGORITHM FOR RECRUITING OF NEURAL TARGETS IN A SPINAL CORD STIMULATOR SYSTEM

CROSS REFERENCE TO RELATED APPLICATIONS

This is a continuation of U.S. patent application Ser. No. 16/737,663, filed Jan. 8, 2020, which is a non-provisional application of U.S. Provisional Patent Application Ser. No. 62/795,268, filed Jan. 22, 2019. These applications are incorporated herein by reference, and priority is claimed to them.

FIELD OF THE INVENTION

This application relates to Implantable Medical Devices (IMDs), and more specifically to techniques for providing stimulation in implantable neurostimulation systems.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a spinal cord stimulation (SCS) system, such as that disclosed in U.S. Pat. No. 6,516,227. However, the present invention may find applicability with any implantable neurostimulator device system.

An SCS system typically includes an Implantable Pulse Generator (IPG) 10 shown in FIG. 1. The IPG 10 includes a biocompatible conductive device case 12 that holds the IPG's circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to proximal contacts 21, which are insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application specific and therefore can vary. The conductive case 12 can also comprise an electrode (Ec). In a SCS application, the electrode lead(s) are typically implanted in the spinal column proximate to the dura in a patient's spinal cord, preferably spanning left and right of the patient's spinal column. The proximal contacts 21 are then tunneled through the patient's tissue to a distant location such as the buttocks where the IPG case 12 is implanted, where they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices discussed subsequently. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by a sequence of waveforms (e.g., pulses) each of which may include a number of phases such as 30a and 30b, as shown in the example of FIG. 2A. Stimulation parameters typically include amplitude (current A, although a voltage amplitude V can also be used); frequency (f); pulse width (PW) of the phases of the waveform such as 30a and 30b; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as an anode (during first phase 30a), and thus sources a positive current of amplitude +A to the tissue. Electrode E2 has been selected as a cathode (again during first phases 30a), and thus sinks a corresponding negative current of amplitude −A from the tissue. This is an example of bipolar stimulation, in which only lead-based electrodes are used to provide stimulation to the tissue. However, more than one electrode may be selected to act as an anode at a given time, and more than one electrode may be selected to act as a cathode at a given time. The case electrode may also be selected as an anode or cathode along with one or more lead-based electrodes, in what is known as monopolar stimulation.

IPG 10 as mentioned includes stimulation circuitry 28 to form prescribed stimulation at a patient's tissue. FIG. 3 shows an example of stimulation circuitry 28, which includes one or more current sources $40_i$ and one or more current sinks $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. PDACs 40$_i$ and NDACs 42$_i$ can also comprise voltage sources.

Proper control of the PDACs 40$_i$ and NDACs 42$_i$ allows any of the electrodes 16 and the case electrode Ec 12 to act as anodes or cathodes to create a current through a patient's tissue, R, hopefully with good therapeutic effect. In the example shown, and consistent with the first phase 30$a$ of FIG. 2A, electrode E1 has been selected as an anode electrode to source current I=+A to the tissue R and electrode E2 has been selected as a cathode electrode to sink current I=−A from the tissue R. Thus PDAC 40$_1$ and NDAC 42$_2$ are activated and digitally programmed to produce the desired current, I, with the correct timing (e.g., in accordance with the prescribed frequency f and pulse width PW). Power for the stimulation circuitry 28 is provided by a compliance voltage VH, as described in further detail in U.S. Patent Application Publication 2013/0289665.

Other stimulation circuitries 28 can also be used in the IPG 10. In an example not shown, a switching matrix can intervene between the one or more PDACs 40$_i$ and the electrode nodes ei 39, and between the one or more NDACs 42$_i$ and the electrode nodes. Switching matrices allows one or more of the PDACs or one or more of the NDACs to be connected to one or more electrode nodes at a given time. Various examples of stimulation circuitries can be found in U.S. Pat. Nos. 6,181,969, 8,606,362, 8,620,436, and U.S. Patent Application Publications 2018/0071520 and 2019/0083796.

Much of the stimulation circuitry 28 of FIG. 3, including the PDACs 40$_i$ and NDACs 42$_i$, the switch matrices (if present), and the electrode nodes ei 39 can be integrated on one or more Application Specific Integrated Circuits (ASICs), as described in U.S. Patent Application Publications 2012/0095529, 2012/0092031, 2012/0095519, 2018/0071516, and 2018/0071513, which are incorporated herein by reference in their entireties. As explained in these references, ASIC(s) may also contain other circuitry useful in the IPG 10, such as telemetry circuitry (for interfacing off chip with telemetry antennas 27$a$ and/or 27$b$), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/0157861.

Referring again to FIG. 2A, the stimulation waveforms as shown are biphasic, with each waveform comprising a first phase 30$a$ followed thereafter by a second phase 30$b$ of opposite polarity. (Although not shown, an interphase period during which no active current is driven may intervene between the phases 30$a$ and 30$b$). Both of the phases 30$a$ and 30$b$ are actively driven by the stimulation circuitry 28 by causing relevant PDACs 40$_i$ and NDACs 42$_i$ to drive the prescribed currents. Biphasic waveforms are useful to actively recover any charge that might be stored on capacitive elements in the current path, such as on the DC-blocking capacitors 38. Charge recovery is shown with reference to both FIGS. 2A and 2B. During the first phases 30$a$, charge will build up across the DC-blocking capacitors C1 and C2 associated with the electrodes E1 and E2 selected to produce the current, giving rise to voltages Vc1 and Vc2. Given the definition of these voltages in FIG. 2B, they are of the same polarity as shown in FIG. 2A. During the second phases 30$b$, when the polarity of the current is reversed at the selected electrodes E1 and E2, the stored charge on capacitors C1 and C2 is recovered, and thus voltages Vc1 and Vc2 return to 0V at the end the second phase 30$b$.

To recover all charge by the end of the second phase 30$b$ of each waveform (Vc1=Vc2=0V), the first and second phases 30$a$ and 30$b$ are charged balanced at each electrode, with the first phase 30$a$ providing a charge of +Q (+A*PW) and the second phase 30$b$ providing a charge of −Q (−A*PW) at electrode E1, and with the first phase 30$a$ providing a charge of −Q and the second phase 30$b$ providing a charge of +Q at the electrode E2. In the example shown, such charge balancing is achieved by using the same phase width (PW) and the same amplitude (|A|) for each of the opposite-polarity phases 30$a$ and 30$b$. However, the phases 30$a$ and 30$b$ may also be charged balance at each electrode if the product of the amplitude and pulse width of the two phases 30$a$ and 30$b$ are equal, or if the area under each of the phases (their integrals) is equal, as is known.

Although not shown, the waveforms may also be monophasic, meaning that there is only one active phase, i.e., only first phase 30$a$ or second phase 30$b$.

FIG. 3 shows that stimulation circuitry 28 can include passive recovery circuitry, which is described further in U.S. Patent Application Publications 2018/0071527 and 2018/0140831. Specifically, passive recovery switches 41$_i$ may be attached to each of the electrode nodes ei 39, and are used to passively recover any charge remaining on the DC-blocking capacitors Ci 38 after issuance of a last pulse phase—i.e., after the second phase 30$b$ if a biphasic pulses are used, or after the sole pulse phase if monophasic pulses are used. Passive charge recovery can be prudent when biphasic pulses are used, because non-idealities in the stimulation circuitry 28 may lead to phases 30$a$ and 30$b$ that are not perfectly charge balanced. Further, passive charge recovery can be necessary when monophasic pulses are used because there is no equal and opposite active phase to recover the charge.

Passive recovery can occur during at least a portion 30$c$ of the quiet periods between the waveforms by closing passive recovery switches 41$_i$. As shown in FIG. 3, the other end of the switches 41$_i$ not coupled to the electrode nodes ei 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 by placing the capacitors in parallel between the reference voltage (Vbat) and the patient's tissue. Note that passive charge recovery is illustrated as small exponentially-decaying curves during 30$c$ in FIG. 2A due to the R-C nature of the circuit, and this current may be positive or negative depending on whether phase 30$a$ or 30$b$ has a predominance of charge at a given electrode. These exponentially-decaying curves would be larger were monophasic pulses used.

FIG. 4 shows an external trial stimulation environment that may precede implantation of an IPG 10 in a patient. During external trial stimulation, stimulation can be tried on a prospective implant patient without going so far as to implant the IPG 10. Instead, one or more trial electrode arrays 17' (e.g., one or more trial percutaneous leads 15 or trial paddle leads 19) are implanted in the patient's tissue at a target location 52, such as within the spinal column as explained earlier. The proximal ends of the trial electrode array(s) 17' exit an incision 54 and are connected to an External Trial Stimulator (ETS) 50. The ETS 50 generally mimics operation of the IPG 10, and thus can provide stimulation to the patient's tissue via its stimulation circuitry 58, which may be equivalent or identical to stimulation circuitry 28 in the IPG 10. The ETS 50 is generally worn externally by the patient for a short while (e.g., two weeks), which allows the patient and his clinician to experiment with different stimulation parameters to hopefully find a stimulation program that alleviates the patient's symptoms (e.g., pain). If external trial stimulation proves successful, the trial electrode array(s) 17' are explanted, and a full IPG 10 and a permanent electrode array 17 (e.g., one or more percutaneous 15 or paddle 19 leads) are implanted as described above; if unsuccessful, the trial electrode array(s) 17' are simply explanted.

Like the IPG 10, the ETS 50 can include one or more antennas to enable bi-directional communications with external devices such as those shown in FIG. 5. Such antennas can include a near-field magnetic-induction coil antenna 56a, and/or a far-field RF antenna 56b, as described earlier. ETS 50 may also include a battery (not shown) for operational power.

FIG. 5 shows various external devices that can wirelessly communicate data with the IPG 10 and the ETS 50, including a patient hand-held external controller 60, and a clinician programmer 70. Both of devices 60 and 70 can be used to wirelessly transmit a stimulation program to the IPG 10 or ETS 50—that is, to program their stimulation circuitries 28 and 58 to produce stimulation with a desired amplitude and timing described earlier. Both devices 60 and 70 may also be used to adjust one or more stimulation parameters of a stimulation program that the IPG 10 or ETS 50 is currently executing. Devices 60 and 70 may also wirelessly receive information from the IPG 10 or ETS 50, such as various status information, etc.

External controller 60 can be as described in U.S. Patent Application Publication 2015/0080982 for example, and may comprise a controller dedicated to work with the IPG 10 or ETS 50. External controller 60 may also comprise a general purpose mobile electronics device such as a mobile phone which has been programmed with a Medical Device Application (MDA) allowing it to work as a wireless controller for the IPG 10 or ETS 50, as described in U.S. Patent Application Publication 2015/0231402. External controller 60 includes a Graphical User Interface (GUI), preferably including means for entering commands (e.g., buttons or selectable graphical icons) and a display 62. The external controller 60's GUI enables a patient to adjust stimulation parameters, although it may have limited functionality when compared to the more-powerful clinician programmer 70, described shortly.

The external controller 60 can have one or more antennas capable of communicating with the IPG 10 and ETS 50. For example, the external controller 60 can have a near-field magnetic-induction coil antenna 64a capable of wirelessly communicating with the coil antenna 27a or 56a in the IPG 10 or ETS 50. The external controller 60 can also have a far-field RF antenna 64b capable of wirelessly communicating with the RF antenna 27b or 56b in the IPG 10 or ETS 50.

Clinician programmer 70 is described further in U.S. Patent Application Publication 2015/0360038, and can comprise a computing device 72, such as a desktop, laptop, or notebook computer, a tablet, a mobile smart phone, a Personal Data Assistant (PDA)-type mobile computing device, etc. In FIG. 5, computing device 72 is shown as a laptop computer that includes typical computer user interface means such as a screen 74, a mouse, a keyboard, speakers, a stylus, a printer, etc., not all of which are shown for convenience. Also shown in FIG. 5 are accessory devices for the clinician programmer 70 that are usually specific to its operation as a stimulation controller, such as a communication "wand" 76 coupleable to suitable ports on the computing device 72, such as USB ports 79 for example.

The antenna used in the clinician programmer 70 to communicate with the IPG 10 or ETS 50 can depend on the type of antennas included in those devices. If the patient's IPG 10 or ETS 50 includes a coil antenna 27a or 56a, wand 76 can likewise include a coil antenna 80a to establish near-field magnetic-induction communications at small distances. In this instance, the wand 76 may be affixed in close proximity to the patient, such as by placing the wand 76 in a belt or holster wearable by the patient and proximate to the patient's IPG 10 or ETS 50. If the IPG 10 or ETS 50 includes an RF antenna 27b or 56b, the wand 76, the computing device 72, or both, can likewise include an RF antenna 80b to establish communication with the IPG 10 or ETS 50 at larger distances. The clinician programmer 70 can also communicate with other devices and networks, such as the Internet, either wirelessly or via a wired link provided at an Ethernet or network port.

To program stimulation programs or parameters for the IPG 10 or ETS 50, the clinician interfaces with a clinician programmer GUI 82 provided on the display 74 of the computing device 72. As one skilled in the art understands, the GUI 82 can be rendered by execution of clinician programmer software 84 stored in the computing device 72, which software may be stored in the device's non-volatile memory 86. Execution of the clinician programmer software 84 in the computing device 72 can be facilitated by controller circuitry 88 such as one or more microprocessors, microcomputers, FPGAs, DSPs, other digital logic structures, etc., which are capable of executing programs in a computing device, and which may comprise their own memories. In one example, controller circuitry 88 may comprise an i5 processor manufactured by Intel Corp., as described at https://www.intel.com/content/www/us/en/products/processors/core/i5-processors.html. Such controller circuitry 88, in addition to executing the clinician programmer software 84 and rendering the GUI 82, can also enable communications via antennas 80a or 80b to communicate stimulation parameters chosen through the GUI 82 to the patient's IPG 10 or ETS 50.

The GUI of the external controller 60 may provide similar functionality because the external controller 60 can include the same hardware and software programming as the clinician programmer. For example, the external controller 60 includes control circuitry 66 similar to the controller circuitry 88 in the clinician programmer 70, and may similarly be programmed with external controller software stored in device memory.

SUMMARY

A method is disclosed for configuring an implantable stimulator device for a patient using an external device in communication with the implantable stimulator device, wherein the implantable stimulator device comprises an electrode array implanted in the patient. In one example, the method may comprise: (a) providing a plurality of selectable options in a user interface of the external device, wherein each selectable option comprises an anatomical target, wherein each anatomical target is associated in the external device with a searching pole configuration configured to recruit that anatomical target and a measurement; (b) receiving an input at the user interface to select one of the anatomical targets; (c) receiving inputs at the user interface to move the searching pole configuration associated with the selected anatomical target to different searching positions in the electrode array; (d) at each of the different searching positions, (i) applying the searching pole configuration associated with the selected anatomical target to the patient, (ii) performing the measurement associated with the anatomical target, and (iii) storing the searching position and its associated measurement in a memory in the external device; and (e) automatically determining at the external device from the stored plurality of searching positions and their associated measurements one or more candidate positions in the electrode array at which a therapeutic stimulation program can be applied to the patient.

In one example, the measurement is configured to gauge the effectiveness of the searching pole configuration at each of the different searching positions. In one example, the measurements associated with the anatomical targets are different for at least some of the anatomical targets. In one example, the searching pole configurations associated with the anatomical targets are different for at least some of the anatomical targets. In one example, the electrode array is implanted in the spinal column of the patient. In one example, the measurement comprises a subjective measurement comprising patient feedback. In one example, the subjective measurement comprises patient feedback concerning how effectively the searching pole configuration addresses a symptom of the patient or produces sequelae at a dermatomal or anatomical location in the patient. In one example, the measurement comprises an objective measurement taken from the patient. In one example, the objective measurement comprises a neural response of the spinal cord. In one example, the objective measurement is taken by the implantable stimulator device. In one example, the objective measurement is taken by a device separate from the implantable stimulator device. In one example, each anatomical target is associated in the user interface with its searching pole configuration and its measurement. In one example, the one or more candidate positions comprise the searching positions where the measurements indicate that the searching pole configuration has been effective for the patient. In one example, the method may further comprising determining a coupling parameter for at least some or all of the electrodes in the electrode array, wherein each coupling parameter is indicative of how well its electrode is coupled to the spinal cord. In one example, the coupling parameter for at least some or all of the electrodes is determined using subjective measurements comprising patient feedback. In one example, the coupling parameter for at least some or all of the electrodes is determined using objective measurements taken from the patient. In one example, in step (e) the one or more candidate positions are also determined using the coupling parameters. In one example, the one or more candidate positions are determined as those for which a variance of the coupling parameters proximate to the searching positions are low. In one example, in step (d)(i), the applied searching pole configuration is modified at the different searching positions in accordance with the determined coupling parameters. In one example, the method may further, in step (d), determining a paresthesia threshold for the searching pole configuration at each of the different searching positions, and in step (d)(iii) storing the searching position and its associated measurement and its associated paresthesia threshold in the memory in the external device. In one example, in step (e), the one or more candidate positions are automatically determined from the stored plurality of searching positions, their associated measurements, and their associated paresthesia thresholds. In one example, the one or more candidate positions comprise the searching positions where the measurements indicate that the searching pole configuration has been effective for the patient and where the paresthesia thresholds are highest. In one example, the method may further comprise determining a coupling parameter for at least some or all of the electrodes in the electrode array, wherein each coupling parameter is indicative of how well its electrode is coupled to the spinal cord, and wherein in step (e) the one or more candidate positions are automatically determined from the stored plurality of searching positions, their associated measurements, their associated paresthesia threshold, and the coupling parameters. In one example, the searching positions comprise a center of an electrical field formed by the searching pole configuration.

A method is disclosed for configuring an implantable stimulator device for a patient using an external device in communication with the implantable stimulator device, wherein the implantable stimulator device comprises an electrode array implanted in the patient. In one example, the method may comprise: (a) providing a plurality of selectable options in a user interface of the external device, wherein each selectable option comprises a searching pole configuration, wherein each searching pole configuration is associated in the external device with a measurement and with a therapeutic stimulation program; (b) receiving an input at the user interface to select one of the searching pole configurations; (c) receiving inputs at the user interface to move the selected searching pole configuration to different searching positions in the electrode array; (d) at each of the different searching positions, (i) applying the searching pole configuration to the patient, (ii) performing the measurement associated with the searching pole configuration, and (iii) storing the searching position and its associated measurement in a memory in the external device; (e) automatically determining at the external device from the stored plurality of searching positions and their associated measurements one or more candidate positions in the electrode array; and (f) applying the therapeutic stimulation program associated with the searching pole configuration at a position in the electrode array that is centered with at least one of the one or more candidate positions.

In one example, the measurement is configured to gauge the effectiveness of the searching pole configuration at each of the different searching positions. In one example, the measurements associated with the searching pole configurations are different for at least some of the searching pole configurations. In one example, the therapeutic stimulation programs associated with the searching pole configurations are different for at least some of the searching pole configurations. In one example, the electrode array is implanted in the spinal column of the patient. In one example, the measurement comprises a subjective measurement comprising patient feedback. In one example, the subjective measurement comprises patient feedback concerning how effectively the searching pole configuration addresses a symptom of the patient or produces sequelae at a dermatomal or anatomical location in the patient. In one example, the measurement comprises an objective measurement taken from the patient. In one example, the objective measurement comprises a neural response of the spinal cord. In one example, the objective measurement is taken by the implantable stimulator device. In one example, the objective measurement is taken by a device separate from the implantable stimulator device. In one example, each searching pole configuration is associated in the user interface with its measurement and its therapeutic stimulation program. In one example, the one or more candidate positions comprise the searching positions where the measurements indicate that the searching pole configuration has been effective for the patient. In one example, the method may further comprise determining a coupling parameter for at least some or all of the electrodes in the electrode array, wherein each coupling parameter is indicative of how well its electrode is coupled to the spinal cord. In one example, the coupling parameter for at least some or all of the electrodes is determined using subjective measurements comprising patient feedback. In one example, the coupling parameter for at least some or all of the electrodes is determined using objective measurements taken from the patient. In one example, in step (e) the one or more candidate positions are also determined using the coupling parameters. In one example, the one or more candidate positions are determined as those for which a variance of the coupling parameters proximate to the searching positions are low. In one example, in step (d)(i), the applied searching pole configuration is modified at the different searching positions in accordance with the determined coupling parameters. In one example, the method may further comprise, in step (d), determining a paresthesia threshold for the searching pole configuration at each of the different searching positions, and in step (d)(iii) storing the searching position and its associated measurement and its associated paresthesia threshold in the memory in the external device. In one example, in step (e), the one or more candidate positions are automatically determined from the stored plurality of searching positions, their associated measurements, and their associated paresthesia thresholds. In one example, the one or more candidate positions comprise the searching positions where the measurements indicate that the searching pole configuration has been effective for the patient and where the paresthesia thresholds are highest. In one example, the method may further comprise determining a coupling parameter for at least some or all of the electrodes in the electrode array, wherein each coupling parameter is indicative of how well its electrode is coupled to the spinal cord, and wherein in step (e) the one or more candidate positions are automatically determined from the stored plurality of searching positions, their associated measurements, their associated paresthesia threshold, and the coupling parameters. In one example, the searching positions comprise a center of an electrical field formed by the searching pole configuration. In one example, the applied therapeutic stimulation program comprises a therapeutic pole configuration that is different from its associated searching pole configuration. In one example, the applied therapeutic stimulation program comprises a therapeutic pole configuration that is the same as its associated searching pole configuration.

BRIEF DESCRIPTION OF THE DRAWINGS

FIG. 1 shows an Implantable Pulse Generator (IPG), in accordance with the prior art.

FIGS. 2A and 2B show an example of stimulation waveforms producible by the IPG or in an External Trial Stimulator (ETS), in accordance with the prior art.

FIG. 9 shows a Graphical User Interface operable in the clinician programmer for implementing the fitting algorithm, and shows a step during which a pole configuration and/or an associated anatomical target can be selected for use during sweet spot searching.

DETAILED DESCRIPTION

Figure 3:
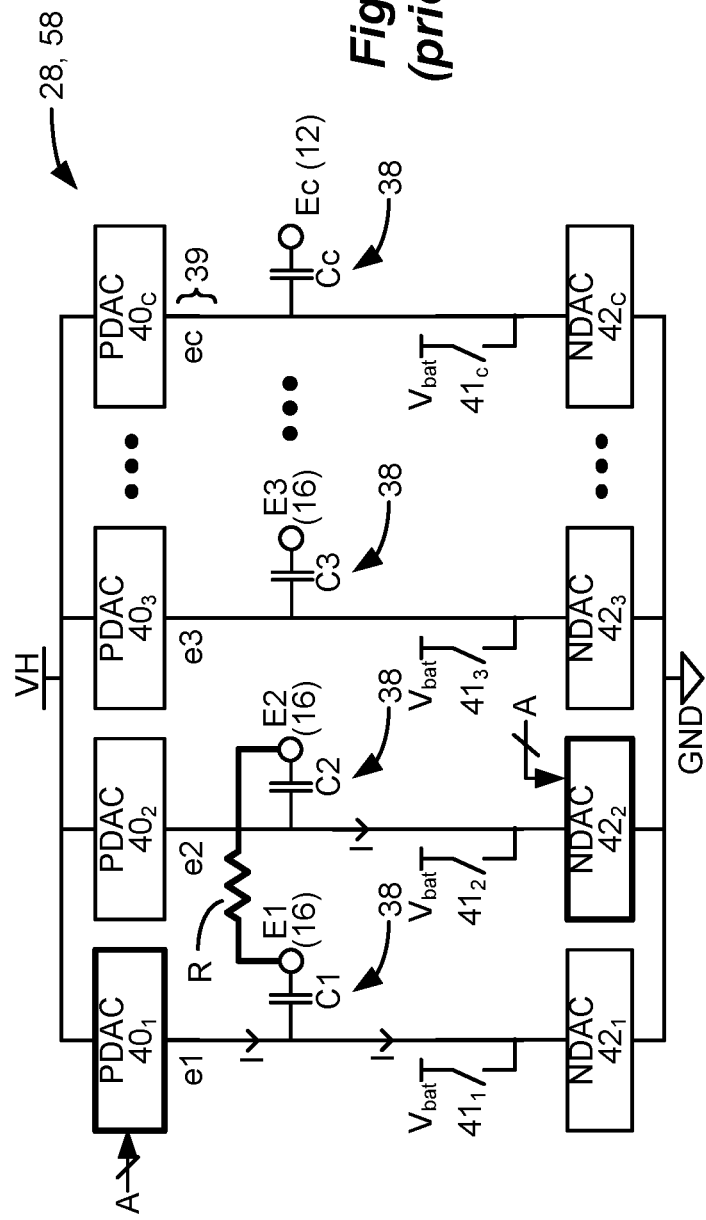
FIG. 3 shows stimulation circuitry useable in the IPG or ETS, in accordance with the prior art.

In an SCS application, it is desirable to determine a therapeutic stimulation program that will be effective for each patient. A significant part of determining an effective stimulation program is to determine which electrodes 16 in the electrode array 17 or 17' should be active, and with what polarities and relative amplitudes, to recruit and thus treat a neural site at which pain originates in a patient. Selecting electrodes proximate to this neural site of pain can be difficult to determine, and experimentation is typically undertaken to select the best combination of electrodes to provide a patient's therapy.

One method for determining where a site of neural pain may be relative to the electrode array 17 or 17', and hence which electrodes should be selected for eventual therapy, is known as "sweet spot" searching. For example, and as explained in U.S. Patent Application Publications 2019/0046800 and 2019/0366104, sweet spot searching can occur by selecting at the clinician programmer 70 a particular pole configuration, and using the clinician programmer to move that configuration around in the electrode array 17 or 17' while receiving feedback from the patient as to which position(s) provides symptomatic (e.g., pain) relief. For example, a bipole configuration can be defined using the clinician programmer 70 at electrodes E1 and E2, with E1 comprising the anode and E2 the cathode, with the patient providing feedback as to how well the bipole at that location "covers" their pain. Thereafter, the bipole can be moved to electrode E2 and E3, with E2 comprising the anode and E3 the cathode, and again with the patient providing feedback at this new bipole location, etc. If the patient's feedback suggests that the E4/E5 bipole is best effective, this may inform the clinician that the site of neural pain is proximate to these electrodes, and therefore that a therapeutic stimulation program can be determined for use by the patient going forward using these electrodes, or electrodes close to them. Both sweet spot searching and the eventual therapeutic stimulation program may be supra-perception, meaning that the patient can feel the stimulation (e.g., paresthesia), or sub-perception, meaning that the patient cannot feel the stimulation (no paresthesia).

The inventors have recognized that different pole configurations are useful in targeting different anatomical targets in the spinal cord. For example, and as discussed later, a bipole configuration is useful to the recruitment of neural fibers in the dorsal horn of the spinal cord. Because the dorsal horn contains inhibitory interneurons which when recruited can inhibit neural conduction, see U.S. Patent Application Publication 2020/0061380, such a bipole configuration is particularly useful in providing therapy which is sub-perception. By contrast, a spread monopole configuration is more useful at recruiting neural fibers in the dorsal roots of the spinal cord, which tends to be supra-perception and thus provides paresthesia. Depending on the circumstances, and perhaps the patient's symptoms, sweet spot searching might benefit from use of different types of pole configurations designed to recruit these different anatomical targets.

The inventors have also recognized that gauging the effectiveness of different pole configurations during sweet spot searching may require different forms of measurements. For example, the effectiveness of pole configurations that are more likely to provide supra-perception stimulation may be best gauged subjectively—that is, by having the patient provide feedback. By contrast, the effectiveness of pole configurations that are more likely to provide sub-perception stimulation may be best gauged objectively by taking measurements from the patient, such as by monitoring neural responses to the applied stimulation. An example of a neural response that can be used to gauge the effectiveness of stimulation can include assessment of Evoked Compound Action Potentials (ECAPs), as explained in U.S. Patent Application Publication 2019/0099602. Having said this, ECAP measurements can be used to assess the effects of supra-perception stimulation as well, as ECAPs are believed to be caused by dorsal column (DC) activation—the same neural elements that are believed to underlie paresthesia. In any event, the type of pole configuration used (and hence the anatomical target chosen) may warrant the use of different types of measurements during the sweet spot search.

Still further, the inventors have recognized that the effectiveness of sweet spot searching can be affected by the degree to which the electrode array is coupled to the spinal cord and other relevant neural targets more generally. Given the complex nature of the environment in which the electrode array 17 or 17' is implanted, some electrodes 16 in the array 17 or 17' may be closer to relevant neural targets than others. This may warrant adjusting the energy (e.g., current) that is provided to different electrodes in a particular pole configuration to ensure the effectiveness of the pole configuration during the sweet spot search. For example, poorly coupled electrodes may be provided larger currents, and well coupled electrodes may be provided smaller currents. Further, an understanding of electrode coupling to neural targets can be useful in gauging the effectiveness of the sweet spot search and in selecting one or more positions in the electrode array 17 or 17' to which an eventual therapeutic stimulation program will be applied.

Figure 6:
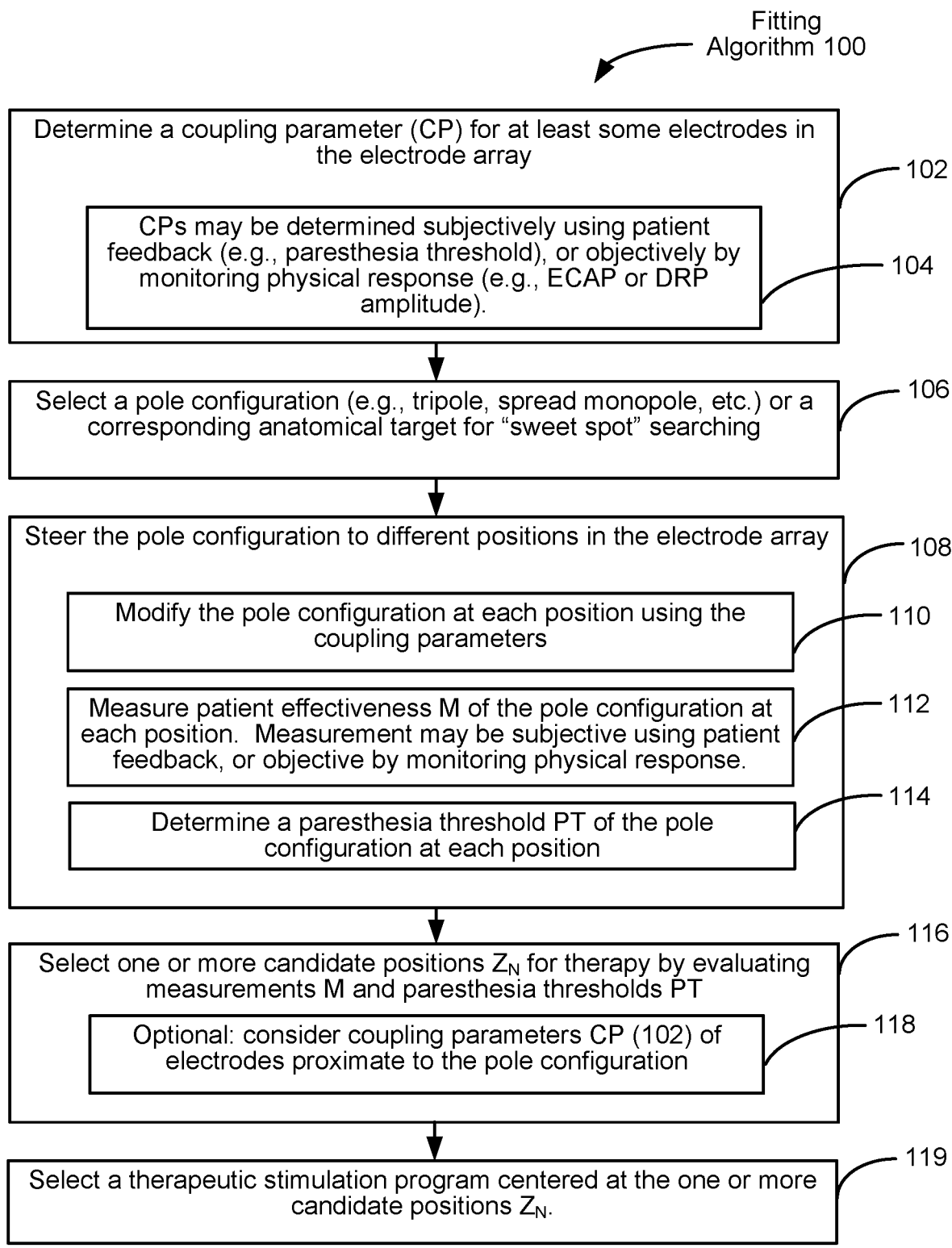
FIG. 6 shows an example of a fitting algorithm operable in a clinician programmer and usable during pole configuration steering to assist in determining candidate positions in the electrode array for receiving therapeutic stimulation programs.

To address these observations, the inventors have devised a fitting algorithm 100, which is summarized in flow chart form in FIG. 6. Various steps of the fitting algorithm 100 are discussed in detail and shown in subsequent figures. While the fitting algorithm 100 preferably includes all steps described in FIG. 6 for optimal performance, individual steps, or subsets of these steps, are also believed to be inventive in their own right. In other words, it is not strictly required in all useful embodiments of the invention that the fitting algorithm 100 includes all described steps.

Figure 4:
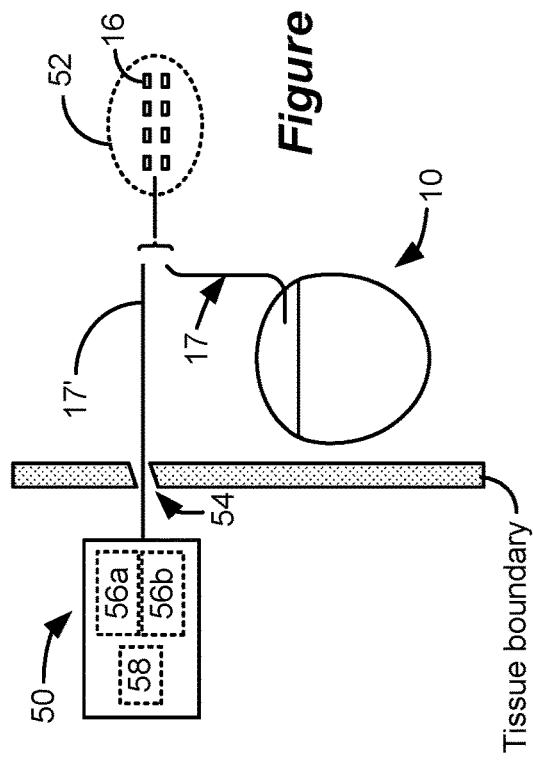
FIG. 4 shows an ETS environment useable to provide stimulation before implantation of an IPG, in accordance with the prior art.

The fitting algorithm 100 is preferably performed on a newly-implanted patient, such as a patient who has had a trial electrode array 17' implanted for use with an ETS 50, or a patient who has received a fully-implanted IPG 10 and electrode array 17 (FIG. 4). That being said, fitting algorithm 100 could be implemented with a patient at any time, as might be useful to determining or adjusting one or more optimal therapeutic stimulation programs for the patient. For example, scar tissue formation, or migration of the electrode array 17 or 17' in the patient, may warrant (re)running the fitting algorithm 100 to adjust a patient's therapeutic stimulation program to one that is more suitable given such changes in physiology over time.

Figure 5:
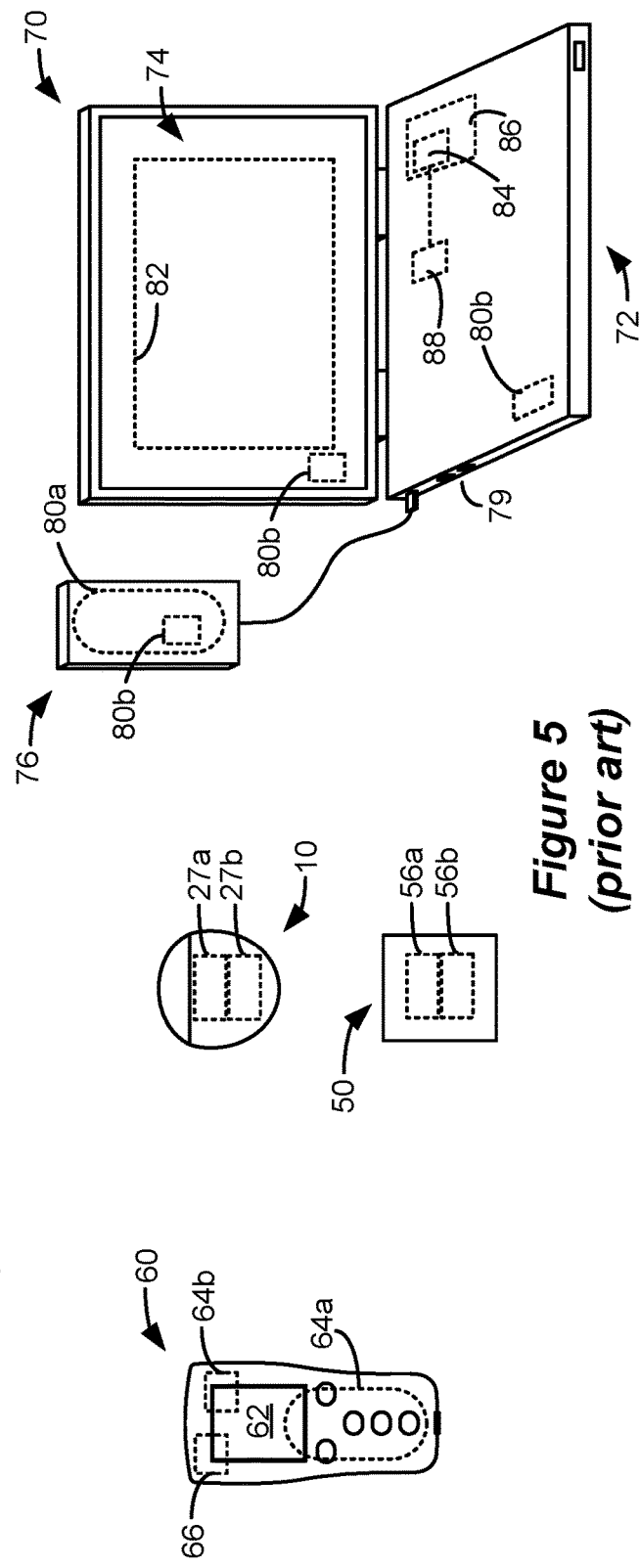
FIG. 5 shows various external devices capable of communicating with and programming stimulation in an IPG and ETS, in accordance with the prior art.

As shown in subsequent figures, the fitting algorithm 100 is preferably implemented on an external device (e.g., a clinician programmer 70; FIG. 5) in communication with the patient's implanted device (IPG 10 or ETS 50), and preferably includes a Graphical User Interface (GUI) 120 rendered on the external device. Alternatively, the fitting algorithm 100 can be implemented on another type of external device, such as the patient's external controller 60 (FIG. 5). The fitting algorithm 100 can comprise a portion of the clinician programmer software 84 described earlier, and executed by the clinician programmer's controller circuitry 88 as described earlier. Aspects of the fitting algorithm 100, including those necessary to render the GUI 120, can comprise instructions stored on a non-transitory computer-readable medium which the controller circuitry 88 can read and execute, such as a magnetic, optical, or solid-state memory. Such memories may be present in the external device (e.g., as memory within or accessible to the controller circuitry 88), or may be loadable into such a device.

In one example, the fitting algorithm 100 in step 102 first determines a coupling parameter (CP) for at least some, and preferably all, of the electrodes 16 in the electrode array 17 or 17'. Said simply, the coupling parameters inform how well each electrode is coupled to the spinal cord or other neural targets. As noted earlier, some electrodes may be closer to the relevant neural targets than others, with closer electrode being well coupled, and farther electrodes being more poorly coupled. The coupling parameters for each electrode are determined in step 102 by providing a stimulus, and monitoring a response to that stimulus. As shown in step 104, such monitoring can be subjective (involving patient feedback) or objective (by measuring a physical response in the patient to the stimulus).

Figure 7:
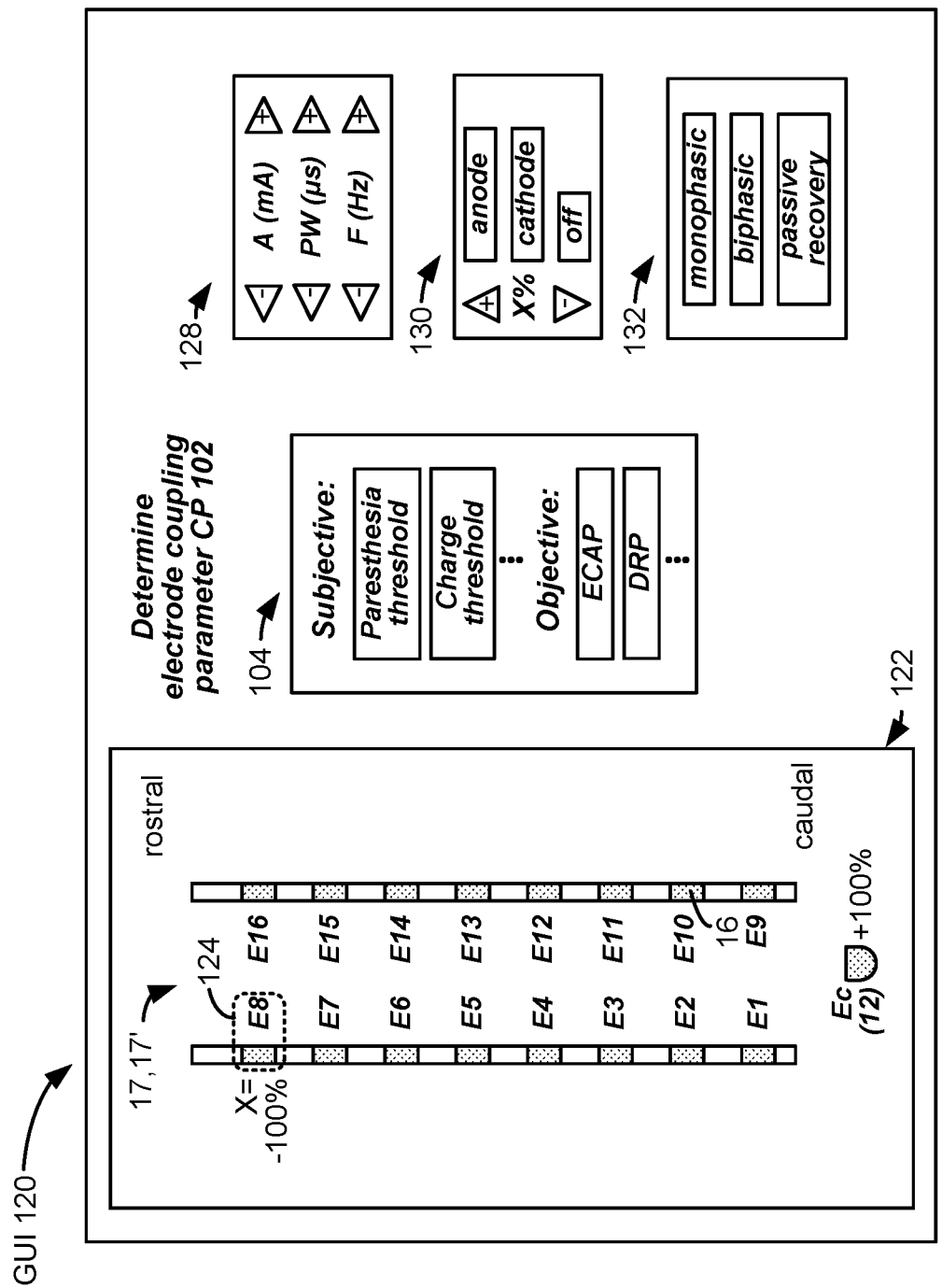
FIG. 7 shows a Graphical User Interface operable in the clinician programmer for implementing the fitting algorithm, and shows a step when coupling parameters are determined for each electrode.

FIG. 7 shows a first example of the GUI 120 rendered on the clinician programmer 70 that can be used to define a stimulus 129 (FIGS. 8A and 8B) used to determine the coupling parameters. A leads interface 122 shows the electrode array 17 or 17', i.e., each of the leads, that is implanted in the patient. In the example shown, two percutaneous leads 15 are shown in the leads interface 122, but a paddle lead 19 (FIG. 1) or other type of lead(s) could be used as well. Although not shown, the leads interface 122 can show the relative position of the leads to each other (e.g., how they are angled or offset from one another), and can show the relative position of the leads to a patient's anatomical structures, such as various vertebrae as determined using fluoroscopic imaging for example. Further, the types of lead(s) that have been used in the patient can be selected in the GUI 120, thus allowing the fitting algorithm 100 to understand the relative size of that lead and the spacing of its electrodes in X and Y directions.

Figures 8A, 8B:
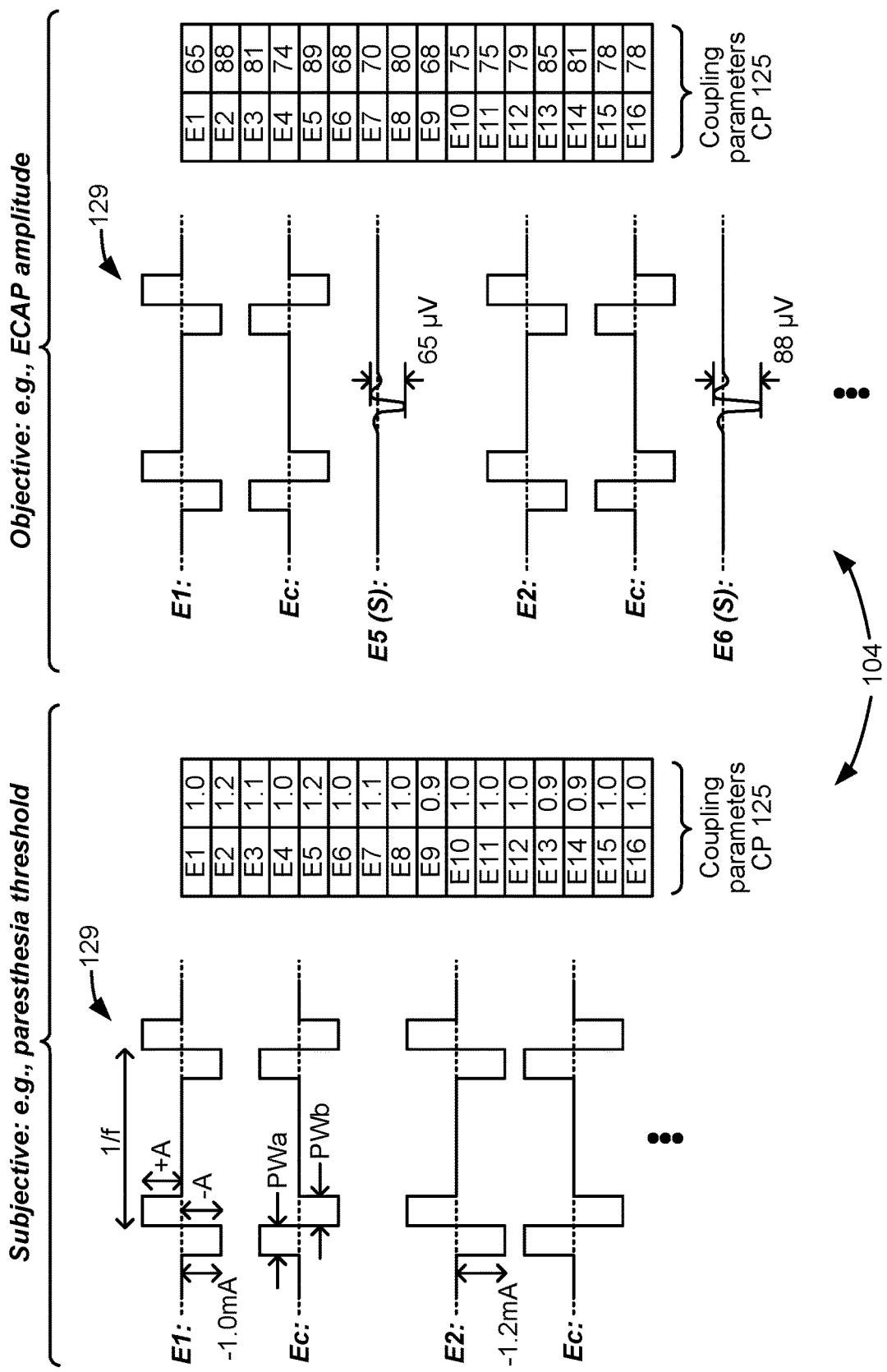
FIGS. 8A and 8B respectively show determination of coupling parameters using subjective and objective measurements.

GUI 120 preferably also includes interfaces useful to define the stimulus 129 used in determining the coupling parameters. For example, parameters interface 128 can be used to define the basic parameters of stimulus 129 (FIG. 8A). Preferably, the stimulus 129 comprises stimulation pulses, similar to those described earlier with reference to FIG. 2A. The parameters interface 128 allows the clinician to adjust for example pulse amplitude (A), pulse widths (PW; or the pulse widths PWa and PWb of individual phases of the pulses), and frequency (f). Many other parameters can be included in parameter interface 128 to shape an appropriate stimulus 129, but only these parameters are shown for simplicity.

A polarity interface 130 can be used to define the polarity of the stimulus 129 at any given electrode, and in this regard, a cursor 124 can be used to select various electrodes 16 as shown in the leads interface. It is seen in the illustrated example that electrode E8 has been selected to act as a cathode (−), and that the case electrode Ec (12) has been selected to act as an anode (+), in what is known as monopolar stimulation. Also present in the polarity interface 130 is an option to specify the amount X % of current—i.e., the fraction of the amplitude A—that is to be provided to each selected electrode. In this example, because there is only one cathode (E8) and one anode (Ec), these electrodes will receive 100% of the total current. That is, E8 will receive a cathodic current of A*−100%=−A, while Ec will receive an anodic current of A*+100%=+A. As will be shown in different examples later, more than one anode electrode and more than one cathode electrode can be selected, and the anodic and cathodic currents can be shared in different proportions by adjusting X in the polarity interface 130.

A waveform phase interface 132 can be used to define the various phases of the stimulus 129, which may be monophasic or biphasic, as explained earlier. Further, the use of passive charge recovery can also be prescribed in waveform phase interface 132. Again, only a basic waveform phase interface 132 is shown for simplicity, but it should be understood that other options could be presented to allow waveforms with more sophisticated phases, or larger numbers of phases, to be defined for the stimulus 129.

Monitoring interface 104 corresponds to step 104 of FIG. 6, and allows for the type of measurement used during coupling parameter determination to be defined. As noted earlier, such measurement may be subjective, involving patient feedback. In one example, the measurement may involve determining a paresthesia threshold at each electrode—e.g., determining a lowest current amplitude A at which stimulation is felt by the patient, as described later with respect to FIG. 8A. Other subjective measurements could also be used and selected. For example, another subject measurement can comprise a lowest amount of total charge (e.g., A*PW) that can be felt by the patient. Still other subjective measures can be used. For example, a constant stimulus can be provided at each electrode, with the patient providing a subjective ranking (e.g., on a scale of 1 to 10) as to the perceived strength of the stimulus 129.

Monitoring interface 104 may also allow the clinician to select an objective measurement to be used during coupling parameter determination. For example, the clinician can select to monitor ECAPs resulting from the stimulus, as described later with respect to FIG. 8B. Still other neural responses can be monitored, such as Dorsal Root Potentials (DRPs), or other objective measurements discussed later.

FIGS. 8A and 8B respectively show examples in which coupling parameters are determined using subjective and objective measurements. In each example, biphasic pulses are used as the stimulus 129, as may be selected in the waveform phase interface 132, although again other types of waveforms could be used for the stimulus 129 as well (e.g., monophasic pulses). Although not shown, passive charge recovery may also be used after the issuance of both pulse phases as described earlier. Further, in this example, the stimulus is monopolar, and is thus presented at a single electrode, using the case electrode Ec (12) as a return path. Again, this isn't necessary, and other types of pulses (e.g., bipolar pulses using two lead based electrodes) could be used for the stimulus 129 as well, for example by designating desired electrodes as anodes or cathodes using the polarity interface 130.

In FIG. 8A, a paresthesia threshold is used as a subjective measurement to determine the coupling parameter at each electrode. Thus, pulses are provided first at electrode E1 (and at return electrode Ec). The amplitude A of the pulse (i.e., the amplitude of either or both of the pulse phases) is gradually increased (using parameter interface 128) until the patient reports perceiving the stimulation. At electrode E1, this paresthesia threshold occurs at an amplitude of 1.0 mA, a value which is stored in a coupling parameter database 125 in the clinician programmer 70's memory. Next, the same pulses are provided to electrode E2, again with increasing amplitude, until the paresthesia threshold (1.2 mA) is determined at this electrode. It is preferred that other pulse parameters (e.g., PW, f) remain constant from electrode to electrode. Note that because the paresthesia threshold is higher (1.2 mA) at E2 than for E1 (1.0 mA), electrode E2 can be said to be more poorly coupled to neural targets than electrode E1, because a higher current is needed at E2 to achieve perceptibility. This process repeats preferably at all other electrodes in the array 17 or 17' (E3, E4, etc.), until the paresthesia thresholds are populated in the coupling parameter database 125.

In FIG. 8B, a particular feature of detected ECAPs—such as the peak-to-peak amplitude—is used as an objective measurement to determine the coupling parameter at each electrode. In this example, pulses are provided to each electrode, and the resulting amplitude of the ECAP is measured. Note in this example that the ECAPs are preferably sensed at electrodes in the array 17 or 17' that don't receive the stimulus 129. Thus, when the pulses are provided to electrode E1, E5 (rostral to E1) is used to sense the ECAPs. By contrast, when pulses are provided to electrode E2, E6 is used to sense the ECAPs. It is desirable to keep the spacing between the stimulating electrode and the sensing electrode constant (e.g., a four-electrode distance). This is because ECAP amplitude varies as a function of distance from the stimulating electrode, and thus keeping a constant spacing ensures that differences in ECAP amplitude are solely due to coupling. If necessary, the rostral-caudal positioning of the sensing electrode can be changed relative to the stimulating electrodes. For example, when a most-rostral electrode E8 is used as the stimulating electrode, a more-caudal electrode E4 can be used as the sensing electrode.

In the depicted example, amplitude (A) and preferably other parameters (PW, f) of the stimulus 129 are kept constant at each of the tested electrodes. The detected ECAP amplitude when E1 receives the stimulus 129 is 65 microvolts, while the sensed amplitude when E2 is stimulated is 88 microvolts. This suggests that E2 is better coupled to the neural target than is E1, because stimulation at E2 invokes a larger response for the same stimulus amplitude. In any event, once all electrodes are tested, the resulting ECAP amplitudes can be stored in the coupling parameter database 125, similar to what occurred when subjective measurements were taken (FIG. 8A). Note that other features of the resulting neural response can be measured and stored as the coupling parameter at each electrode. For example, and as explained in U.S. Patent Application Publication 2019/0099602, other features of the ECAP (e.g., its area, length, other peak heights, etc.) can also be used as objective measurements. In another example, the stimulus 129 provided to the electrodes may not be constant. For example, the stimulus can be adjusted (e.g., its amplitude A) until an ECAP of a certain amplitude threshold (e.g., 70 microvolts) is detected, with the amplitude of that stimulus stored as the coupling parameter. Although not shown, note that coupling parameters as stored in database 125 may be normalized in magnitude.

Coupling parameter measurements in steps 102 and 104 can occur in still different ways, and U.S. Patent Application Publication 2018/0214689, which is incorporated herein by reference, can also be used.

Referring again to FIG. 6, after determining and storing the coupling parameters, the fitting algorithm 100 can next proceed to step 106, which allows the user to select a pole configuration and/or an anatomical target to be used during sweet spot searching. FIG. 9 shows an example of the GUI 120 at this step. Shown is a table 131 that informs the clinician of the types of anatomical targets that can be recruited during the sweet spot search; a searching pole configuration suitable for recruiting that target and that can be moved to different positions in the array 17 or 17'; aspects related to how the effectiveness of the pole configuration can be measured (M) at each position during the sweet spot search; and, optionally, a default therapeutic stimulation program that may be used by the clinician after the sweet spot searching is completed. All or parts of table 131 can be stored in memory in the clinician programmer 70 so that they may be retrieved and displayed once the GUI 120 has reached step 106 of the fitting algorithm. In the illustrated example, each row is selectable by the clinician to automatically define the manner in which sweet spot searching will occur.

Table 131 can be arrived by experimentation or by an understanding of neural physiology—i.e., by understanding which anatomical targets are best or most logically recruited by particular pole configurations. Similar experimentation or understanding can be used in table 131 to associate an anatomical target or pole configuration with a best type of measurement (e.g., subjective or objective), and further with a best therapeutic stimulation program to be used after sweet spot searching. The data in table 131 may be updated in the clinician programmer 70, and as reflected in GUI 120, from time to time as new correlations are learned between different anatomical targets, pole configurations, measurement aspects, and default therapeutic stimulation programs.

The point of table 131, and as reflected in GUI 120, is to assist the clinician during the sweet spot search. Table 131 takes much of the guess work out of sweet spot searching in terms of the anatomical target to be recruited, the pole configuration best suited to recruit that anatomical target, and the measurements that are best made to gauge effectiveness.

In table 131, the default pole configuration to be used during sweet spot searching comprises a pole definition (e.g., a tripole, bipole, spread monopole), and examples of these types of pole definitions are shown in subsequent drawings. Also shown are a default current fraction and position of each pole in the pole configuration. In FIG. 9, the current fractions of each pole are shown as a percentage of total amplitude A otherwise specified (see FIGS. 10A-10D), with positive percentages representing a percentage of anodic current, and negative percentages representing a percentage of cathodic current.

Figure 10A:
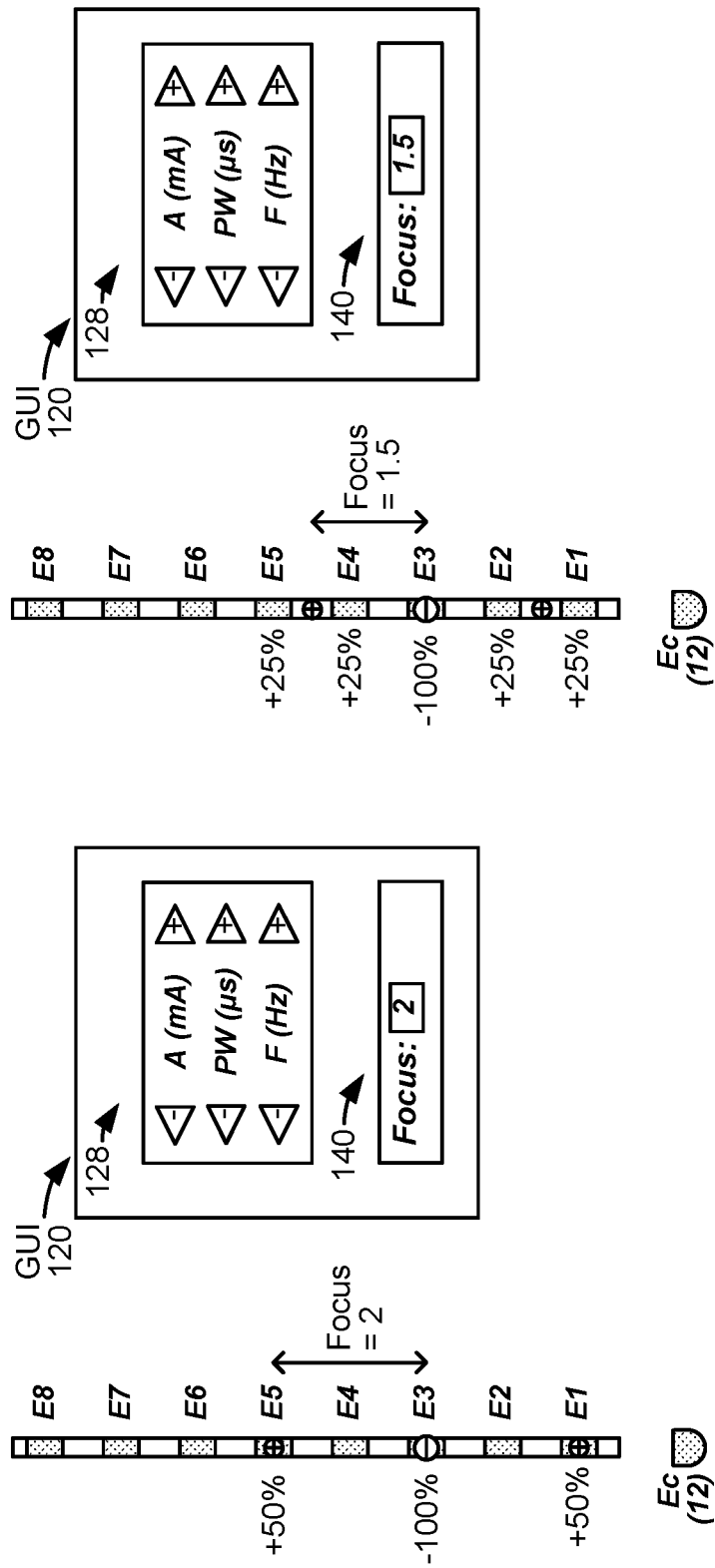
FIGS. 10A-10D shows different examples of selected pole configurations designed to recruit different anatomical targets, or that use different types of measurements to gauge pole configuration effectiveness at different positions in the electrode array.

For example, assume a tripole is selected as is useful to recruiting neural targets in the dorsal column, or conversely that the dorsal column is selected thus giving rise to a default tripole configuration (rows 1 and 2). As shown in the table 131 in FIG. 9, two anode poles will be formed in the electrode array 17 or 17', with each receiving 50% of the anodic current (+50%*A), and a single cathode pole will be formed which will receive 100% of the cathodic current (−100*A). The position of each pole in the electrode array 17 or 17' is shown in parentheses relative to a center point (0) of the pole configuration. In this example, the position comprises an electrode spacing, with positive numbers showing the position of the pole rostrally relative to the center, and with negative numbers showing the position of the pole caudally relative to the center. Assume a tripole is centered at electrode E3, as shown in FIG. 10A. This places the single cathode pole (−100(0)) at E3. The two anode poles will then be placed at E5 (+50(+2)) rostral to E3, and E1 (+50(−2)) caudal to E3. Pole position may alternatively comprise an absolute measurement (e.g., in millimeters), which is not difficult for the fitting algorithm 100 to handle because the spacing of the physical electrodes 16 in an array 17 and 17' can be easily known by virtue of the types of lead(s) that have been used for the patient.

FIG. 10A as just noted shows an example in which dorsal column/tripole has selected, and centered at E3. The GUI 120 can allow for adjustments from the default values for the pole configuration provided by table 131. For example, the parameters interface 128 can be used to adjust basic waveform parameters (e.g., A, PW, f). Additionally, the "focus" of the tripole can be adjusted, which defines the positions of the anode poles relative to the central cathode pole. In the example shown, the focus is again represented by an electrode spacing number (e.g., 2), but could also be expressed in absolute terms (e.g., as millimeters). The focus of the tripole may be adjusted using a focus interface 140, and to the right in FIG. 10A the focus has been adjusted to 1.5 electrodes, which places the anode poles at positions between E5 and E4, and between E2 and E1.

In this regard, note in the disclosed technique that poles in the pole configuration do not need to always be positioned at the physical positions of the electrodes. When the position of a pole is set in the GUI 120, an electrode configuration algorithm (not shown) in the clinician programmer 70 can compute what physical electrodes should be active, and with what polarities and current fractions, to best form the pole at the desired position. The reader is assumed familiar with this electrode configuration algorithm, and it is described further for example in U.S. Patent Application Publication 2019/0175915, which is incorporated herein by reference. Thus, the electrode configuration algorithm in FIG. 10A operates to automatically select the active electrodes necessary to position the anode poles at positions between the electrodes. For example, the anode pole between E5 and E4 is prescribed to receive 50% of the anodic current. As a result, the electrode configuration algorithm activates both of electrodes E4 and E5, but shares the anodic current between them (+25%*A each) to in effect create a virtual anode pole between E4 and E5. Likewise, the electrode configuration algorithm would prescribe currents of +25%*A at each of electrodes E1 and E2 to form the desired +50*A anode pole at the position between E1 and E2.

Figure 10C:
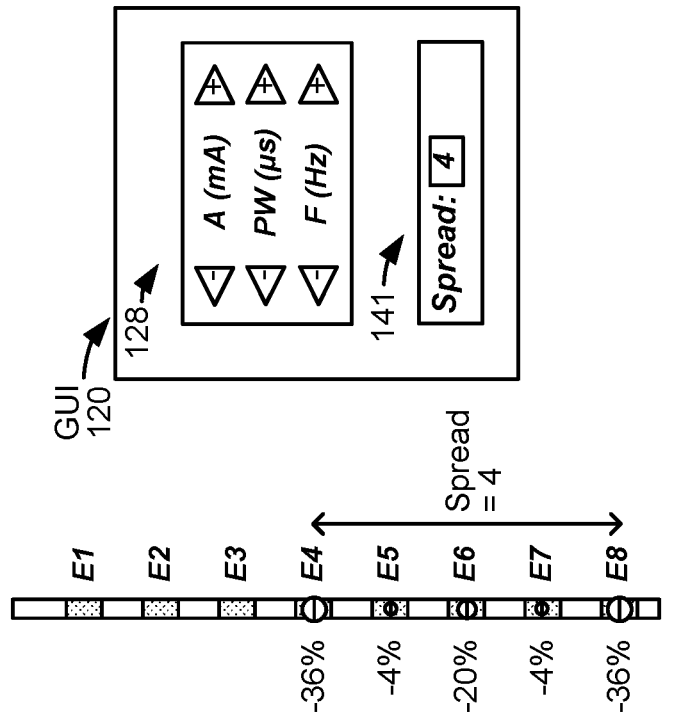
Figure 10B:
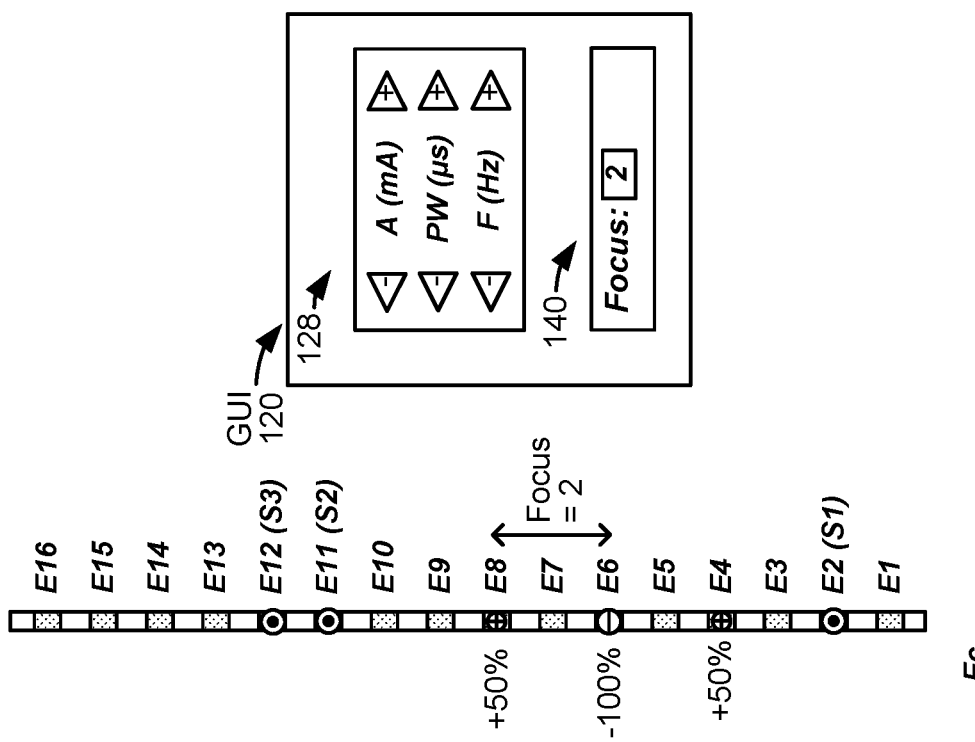
Figure 10D:
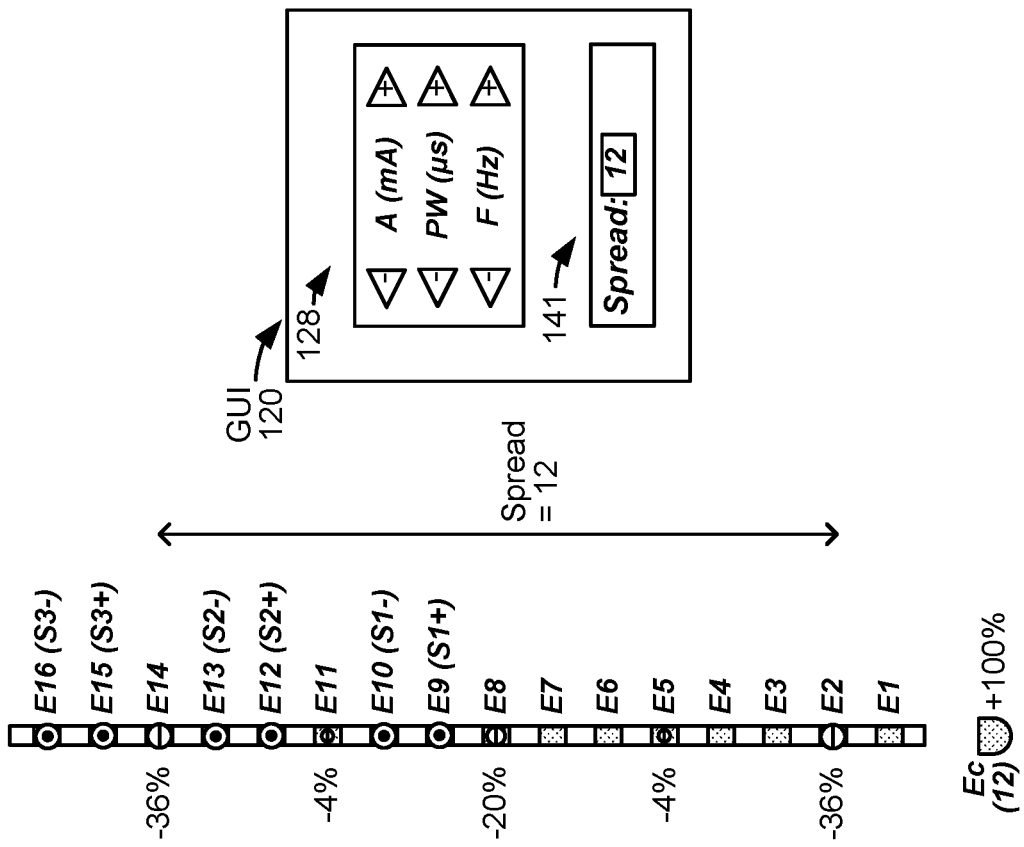

Rows 1 and 2 in table 131 prescribe a tripole to recruit the dorsal column, but prescribe different measurements to gauge effectiveness. In row 1, subjective measurements are used, as explained later with respect to FIGS. 11A-11C. In row 2, objective measurements are used, specifically a feature of ECAPs (e.g., amplitude, although other features can also be used as explained above) that result from the pole configuration, as explained later with reference to FIG. 12. In this objective measurement example, table 131 preferably automatically defines the sense electrode(s) that are to be used in sensing the ECAP amplitude. Again, these sense electrodes are denoted by an electrode spacing relative to the center of the tripole, but again could comprise an absolute measurement. Thus, when sensing ECAPs in this example, one or more of electrodes spaced rostrally from the center (+5, +6) can be used, and one or more electrodes spaced caudally (e.g., −4) can be used. This is shown in FIG. 10B, where it is assumed that the tripole (i.e., the cathode pole) is centered at E6. The anode poles in this example appear at E8 (+2) and E4 (−2). Sensing electrode S3 appears at E12 (+6 relative to center E6), sensing electrodes S2 appears at E11 (+5), and sensing electrode S1 appears at E2 (−4). Note that as the tripole as is subsequently moved, some sensing electrodes will be inaccessible. For example, if the center of the tripole is moved to E3, there will be no room to accommodate sensing electrode S1. Should this occur, other sensing electrodes that can be accommodated may be used (S2 and S3), or the rostral-caudal nature of the sensing electrodes can be changed (e.g., S1 can be changed from −4 to +4). Note that table 131 could prescribe that sensing occur using one or more electrodes on a different lead in the array 17 or 17' as well (not shown).

Rows 3-4 in table 131 prescribe a spread monopole known to be effective in recruiting the dorsal roots of the spinal cord. This spread monopole is shown in FIG. 10C. In this example, the spread monopole comprises a spread cathode, with the cathodic current fractionalized between five different adjacent electrodes in the array 17 or 17', with the central cathode pole receiving 20% of the cathodic current (−20%*A), next adjacent cathode poles receiving 4% (−4%*A), and still next adjacent cathode poles receiving (−36%*−A), for a total of −100*A. The case electrode Ec (12) acts as a return, and thus receives 100% of the anodic current (+100%*A). This spread monopole provides a larger electric field in the tissue as is useful for the recruitment of dorsal roots. Note that a spread interface 141 can be used to adjust the spacing of the poles in the spread monopole, which by default is set to an electrode spacing of 4.

Rows 3-4 are each associated with different types of measurements that will be used during sweet spot searching to gauge the effectiveness of the spread monopole. In rows 3 and 4, subjective measurements are used reliant on patient feedback. In row 3, the patient will provide input regarding paresthesia, whether stimulation can be felt, or how strongly the stimulation feels. In row 4, the patient will provide input regarding proprioception, i.e., how or where the patient senses stimulation.

In row 5 of table 131, a wider-spread monopole (with a spread of 12) is prescribed, again as useful to recruiting the dorsal roots of the spinal cord. However, in this example, effectiveness is gauged objectively by detecting the amplitude or other feature of dorsal root potentials (DRPs). In this example, shown in FIG. 10D, sensing of the DRPs can occur differentially using pairs of electrodes (Si+, Si−), using for example first and second rostral electrodes from the center of the spread monopole (S1+, S1−), or fourth and fifth rostral electrodes (S2+, S2−), etc.

Rows 6 and 7 target still different neural structures using different pole configurations, and further illustrate that effectiveness can be objectively measured using devices external to the IPG or ETS—that is, without sensing a neural response at the electrodes of those devices. For example, in row 6, a spread bipole is used to gauge an overall effect not particular to any specific neural target, and uses an Electroencephalogram (EEG) on the scalp to gauge effectiveness. The spread bipole produces a strong but generally uniform electric field along the axis of the bipole (e.g., rostrocaudally), and is useful because certain neural elements in the spinal cord, such as inhibitory interneurons and descending terminals, are oriented rostrocaudally and "end" segmentally. Ends that point rostrocaudally are sensitive to uniform and strong parallel fields, while axons of passage (such as the dorsal columns) are not sensitive to these fields and are therefore "bypassed" by the stimulation. EEG can be a useful measure of effectiveness here because the effects of stimulation (beyond potentially pain relief) due to subperception therapy may not be immediately felt by the patient, as the spread bipole would theoretically not activate dorsal column fibers responsible for generating sensations and paresthesia. In row 7, a bipole is used to target the dorsal horn and ventral roots, and uses Electromyography (EMG) sensing at a patient's right and left legs to gauge effectiveness.

Although not shown in FIG. 9, table 131 can include further information about the directionality of the pole configuration, and/or its measurement, as can be effected using leads having directional characteristics, such as split ring electrodes. See, e.g., U.S. Patent Application Publication 2020/0001091 (describing the production of directional electric fields in tissue using split-ring electrodes). Options having directionality aspects may not be displayed in table 131 if electrodes lacking directionality are used with the patient. Further, it should be understood generally that the selectable rows in table 131 can depend, and can be automatically populated, as a function of the type of leads used (e.g., the number of electrodes, whether the electrodes are split ring), the type of IPG 10 or ETS 50 used (e.g., do they support measuring of neural responses such as ECAPs and DRPs), and the type of measurement equipment (e.g., EEG, EMG, etc.) supported by use with the system. In other words, these factors may automatically limit the options presented in table 131.

Once step 106 has been completed, and a searching pole configuration/anatomical target selected, fitting algorithm 100 can proceed to step 108, where the pole configuration is steered to different positions in the electrode array 17 or 17'. As shown in FIG. 6, this can involve modifying the pole configuration using the coupling parameters determined earlier in step 102 (110); measuring the effectiveness (M) of the pole configuration at each position (112); and determining a paresthesia threshold (PT) at each position (114).

Figure 11A:
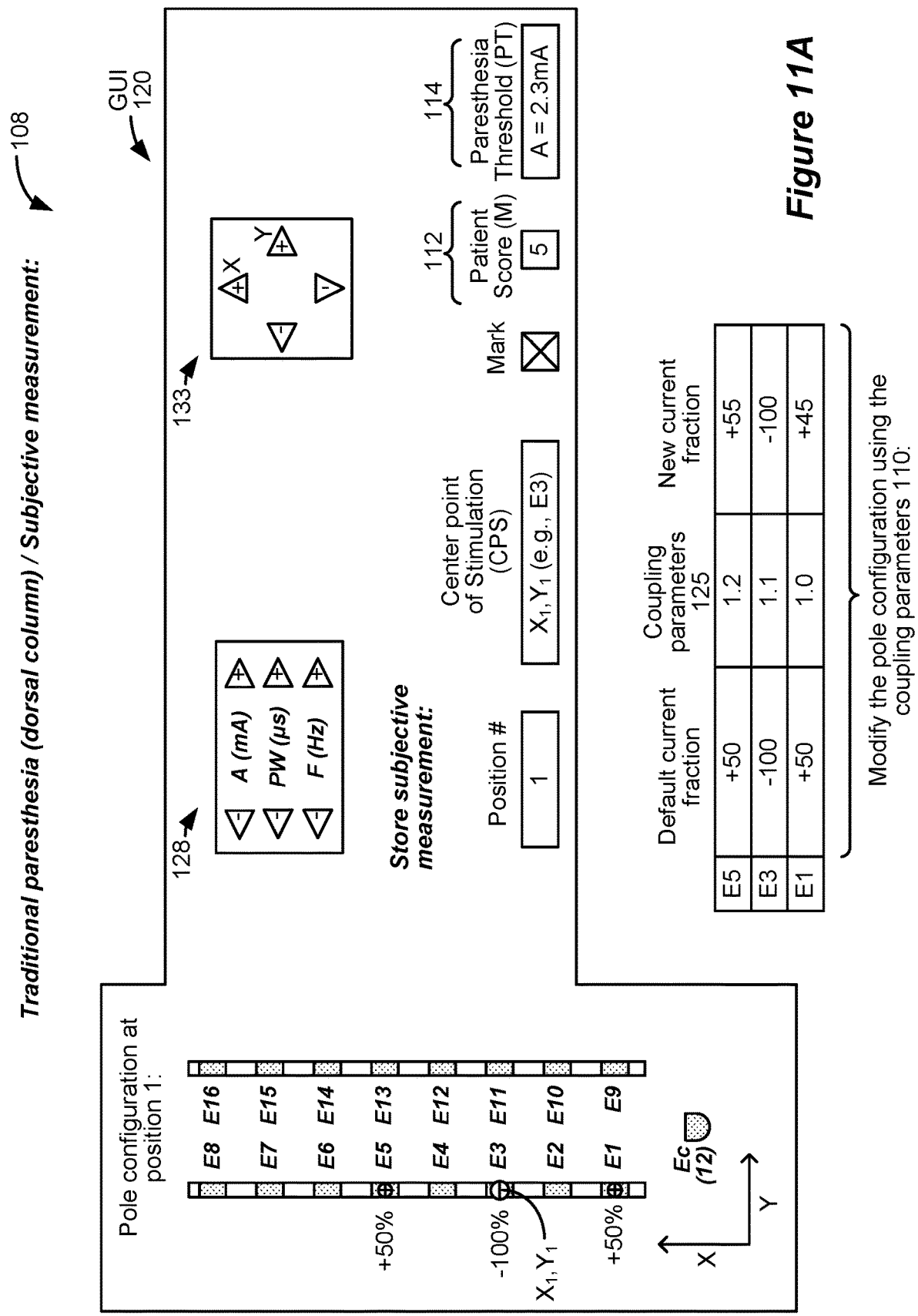
FIGS. 11A-11C show examples in which a tripole configuration designed to recruit neural targets in the dorsal column is steered to different position in the electrode array, and shows recording of different subjective measurements of effectiveness at each position, as well as a paresthesia threshold at each position.
Figure 11B:
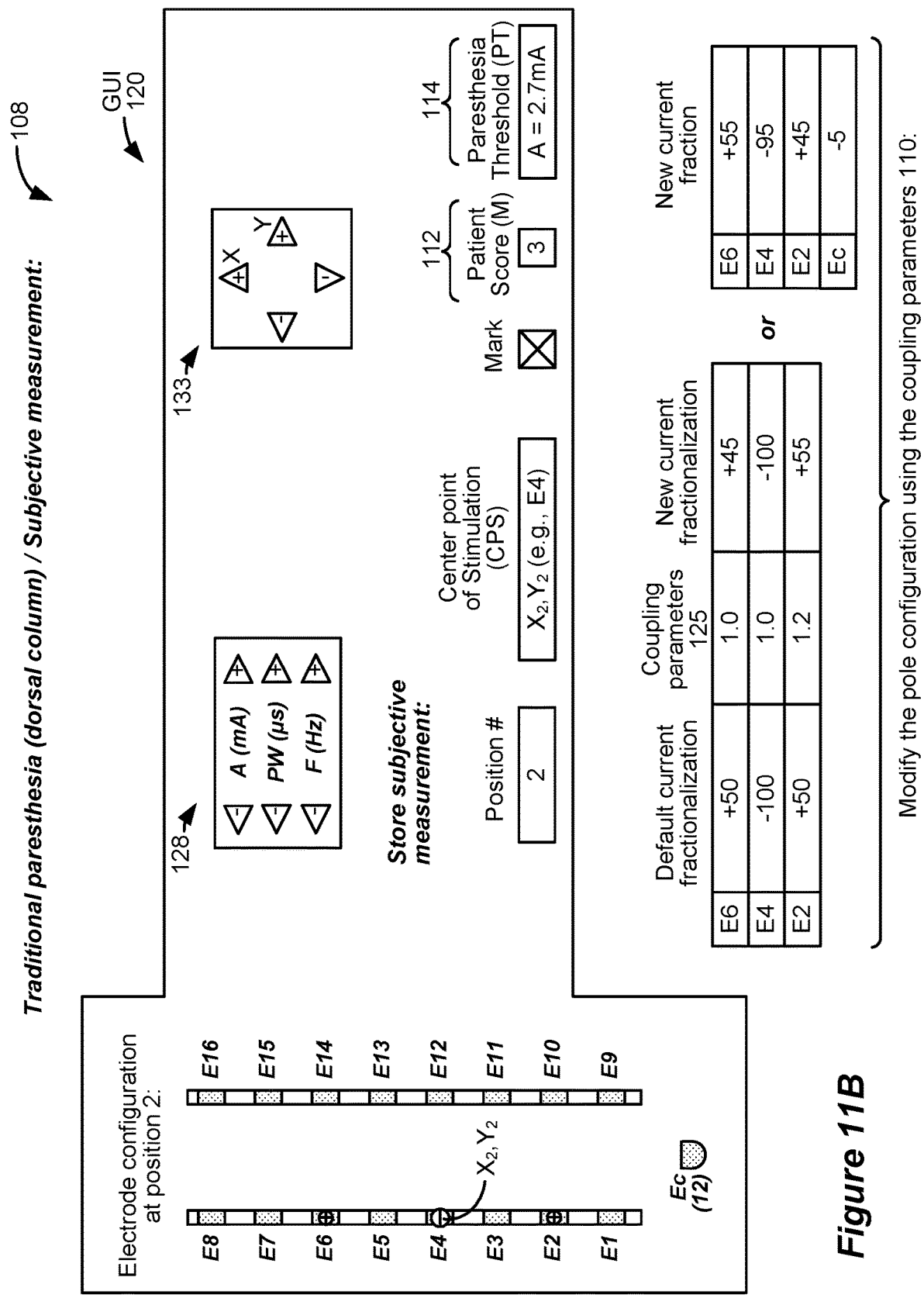
Figure 11C:
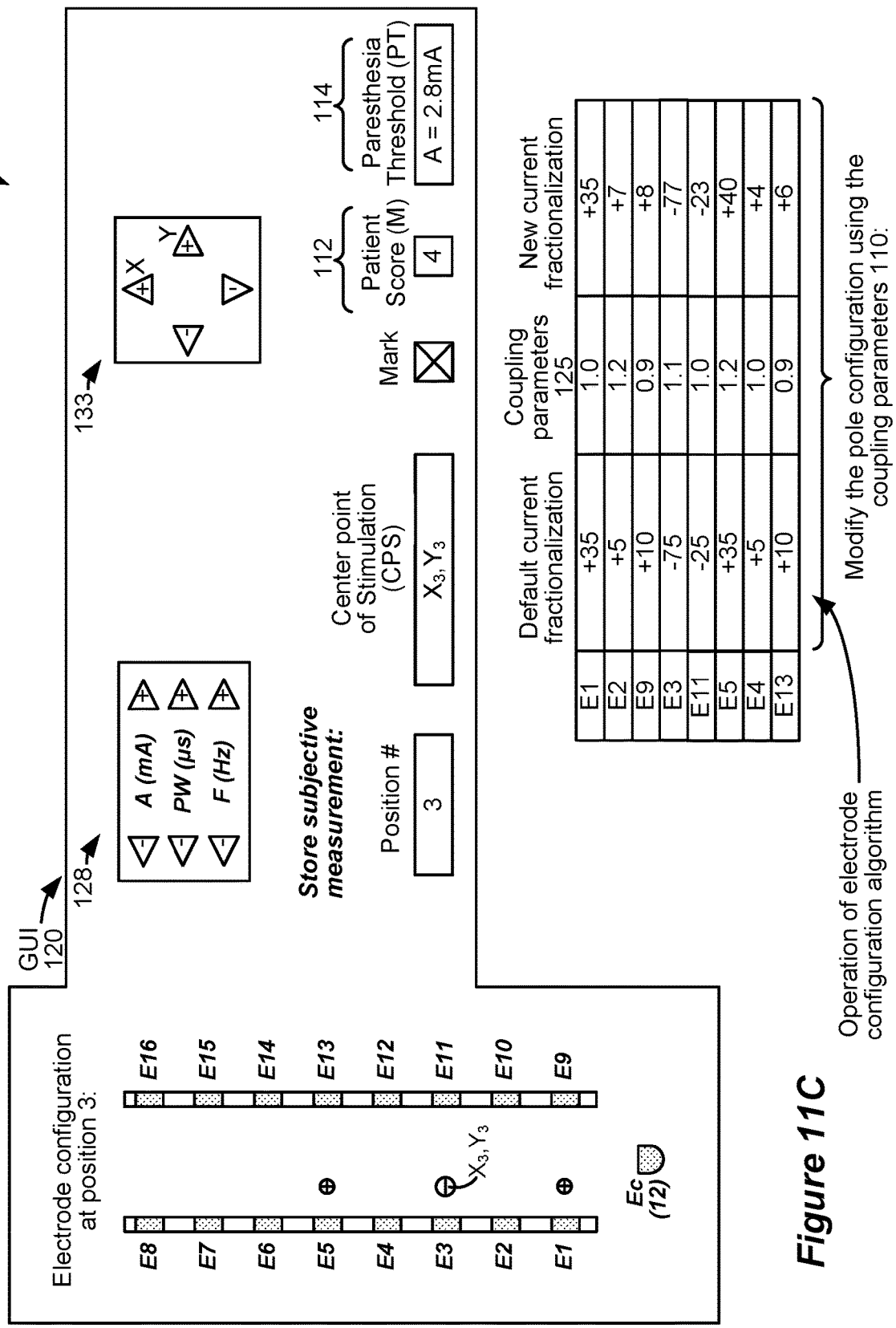

FIGS. 11A-11C show a first example of pole configuration steering 108, which assumes that the clinician has earlier selected from table 131 (FIG. 9) to use a tripole during steering to recruit the dorsal column as an anatomical target. Further, it is assumed in this example that the clinician has selected row 1 in the table 131, and therefore that the measurements (M) taken during steering involve a subjective measurement from the patient. In this example, the measurements include a pain score provided by the patient, although other subjective measurements could also be used. Subjective measurements need not necessarily relate to how well the searching pole configuration addresses a symptom of the patient. For example, subject measurements can also indicate how well or to what extent the searching pole configuration produces sequelae at a dermatomal or anatomical location in the patient.

FIG. 11A shows the selected tripole at a first position (position 1). Pole configuration position can be denoted in different manners, but in one example the position may comprise a point in the array 17 or 17' that comprises a central point of stimulation (CPS) of the pole configuration, for example a center point of the electric field created in the tissue. In the example of a tripole, this central point can comprise the position of the sole cathode, and so in FIG. 11A, the tripole's position can be said to be at electrode E3. More generally, and because the electrode array 17 and 17' can be two dimensional—such as if more than one percutaneous lead is used, or if a paddle lead is used—the CPS can comprise a X,Y coordinate. At position 1, the CPS is $X_1,Y_1$, which again comprises the center of electrode E3. Different pole configurations would have different CPSs. For example, a bipole would have a CPS between the anode and cathode poles, etc. The center point of the electric field can be determined in different ways. It can for example comprise a geometric center, a point at which the electric field is the strongest (maximum dV/dt), a point at which its rate is changing the fastest (maximum $d^2V/dx^2$), or other significant points of the electric field.

At each position, and in accordance with step 110 (FIG. 6), the pole configuration is preferably modified in accordance with the electrode coupling parameters determined earlier in step 102. This step 110 is optional, but is preferred to "normalize" the effect of the pole configuration at each position. Modification of the pole configuration is shown at the bottom of FIG. 11A, and involves scaling the default current fractions specified in table 131 (FIG. 9). For example, FIG. 11A involves use of a tripole with a default +50/−100/+50 current fractionalization, as described earlier. At position 1, electrodes E1, E3, and E5 are involved in forming the poles in the pole configuration. The coupling parameters for these electrodes—as stored in database 125 (FIG. 8A) for example, which are representative of a paresthesia threshold—are 1.0, 1.1, and 1.2 respectively. (Again, objective measurements such as shown in FIG. 8B could also have been used). As such, the default current fractions can be changed at these electrodes during step 110. Anode pole E5 has a higher coupling parameter than anode pole E1, meaning that E5 is more poorly coupled to the spinal cord than is E1. Step 110 can therefore automatically increase the current fraction at electrode E5 relative to E1 to compensate for the difference. For example, the anodic currents at E5 and E1 can be weighted in accordance with their coupling parameters: the coupling parameters at these electrodes can be added (2.2), with E5 adjusted to receive an anodic current of +55% in accordance with its coupling parameter (e.g., 1.2/2.2), and with E1 adjusted to receive an anodic current of +45% (e.g., 1.0/2.2). This is just one example of how the current fractions for the steering pole configuration from table 131 can be modified in light of the coupling parameters at each electrode, and other mathematical means of adjustment are possible.

Once the pole configuration is adjusted (110) to account for difference in the electrode coupling parameters, the adjusted pole configuration is transmitted to the IPG or ETS to be applied to the patient, and one or more measurements (M) of the effectiveness of the pole configuration at this position can be recorded and stored in the system (step 112; FIG. 6). In this example, a subjective measurement is obtained from the patient, such as a pain score rated on a scale of 1 to 10 (with 10 comprising the least pain, and 1 the highest). Other subjective measurements are possible. For example, the patient can be asked to describe a percentage to which the pole configuration at position 1 seems to be covering his pain. The measurements may also be inverted, with lower scores indicating a better patient result. In any event, once obtained from the patient, the subjective patient score measurement (M) can be entered by the clinician in the GUI 120 as shown. Although not shown, note that there can be more than one subject measurements made in step 112. Multiple measurements at each position can be averaged, weighted and summed, or a best measurement chosen, to arrive at a single measurement. Alternatively, each measurement can be independently tracked and evaluated, as described later.

At step 114 (FIG. 6), it is preferable (but not strictly necessary) to also determine a paresthesia threshold (PT) of the pole configuration at each position, and to record this paresthesia threshold in the GUI 120 for storage and later consideration. This paresthesia threshold PT comprises a lowest level at which the patient can feel stimulation as provided by the entirety of the entire pole configuration, which again may comprise a current level. Note that the paresthesia threshold PT determination at this step is gauged using the entire pole configuration, and as such is different from determination of the per-electrode coupling parameter (CP) described earlier (step 102) (which can also be determined using a paresthesia threshold; e.g., FIG. 8A). When determining the paresthesia threshold PT of the pole configuration, the clinician may vary the total amplitude A in the GUI 120, for example at parameters interface 128, which will vary the current provided to the various poles in the pole configuration in accordance with their current fractions. As described later with reference to FIGS. 13A and 13B, the paresthesia thresholds PT are useful to determining candidate positions at which actual therapeutic stimulation programs can be applied to the patient once sweet spot searching has finished.

As shown, the GUI 120 can include an option to mark the present position of the pole configuration as one at which a measurement M and paresthesia threshold PT will be taken and stored. This is useful, as it can allow the clinician to experimentally move the pole configuration to different positions (as described below) without necessarily or automatically recording a measurement and paresthesia threshold at every new position; some pole configurations positions may not provide useful data, or have such a poor patient measurement M that they are not worth recording.

After recording at least one measurement M of pole configuration effectiveness at position 1, and preferably also recording the paresthesia threshold PT at that position, the pole configuration can be moved (steered) to a new location in the electrode array 17 or 17'. Moving of the pole configuration to a new position can be effected using the GUI 120 provided by the clinician programmer 70. For example, as shown in FIG. 11A, a position interface 133 can be used to move the pole configuration in X or Y positions within the array 17 or 17'. Alternatively, the clinician programmer 70 can include other user interface elements. For example, the clinician programmer 70 can include a joystick (not shown) or other attachment to the clinician programmer to allow the position of the pole configuration to be moved in the array. Preferably, the position of the poles as moved is shown on a depiction of the electrode array 17 or 17' so that they can be understood in context.

FIG. 11B shows that the tripole configuration has been moved to a new position (position 2) which is up rostrally by one electrode, such that the tripole (its cathode pole) is now centered at $X_2, Y_2$ (e.g., E4), with the anode poles at electrodes E6 and E2. As before the pole configuration can be modified (110) to compensate for the coupling parameters (CP) at the electrodes used in forming the poles. Because anode pole E6 is better coupled than anode pole E2, the current fraction provided to E2 can be increased (+55) relative to E6 (+45). In another alternative, because the single cathode pole E4 is better coupled than the average of the anode poles E2 and E6, part of the cathodic current can be moved from the cathode pole E4 (−95) to the case electrode Ec (−5). Again, mathematical weighting can be used to determine how to modify the pole configuration using the coupling parameters (110). Once the modified pole configuration is applied at position 2 (and upon marking this position if necessary), its position ($X_2, Y_2$), the relevant patient measurement M, and the paresthesia threshold PT can be recorded, and the pole configuration then moved (133) to a different position.

FIG. 11C shows the tripole moved to a third position (position 3), and is interesting because in this circumstance the poles in the tripole do not correspond to the physical positions of the electrodes. As noted earlier, an electrode configuration algorithm can be used to compute what physical electrodes will be active, and with what polarities and current fractions, to best form the poles at the desired position. In this example, the electrode configuration algorithm has determined that electrodes E1, E2, E3, E4, E5, E9, E11, and E13 should be active, and with current fractions +35, +5, −75, +5, +35, +10, −25, +10 respectively to position the poles of the prescribed +50/−100/+50 tripole at the desired positions. Thereafter, this default current fractionalization may again be modified (110) based on the coupling parameters 125 to a new fractionalization at these electrodes. At this new position ($X_3, Y_3$), a new patient measurement M and paresthesia threshold PT can be determined and stored, and so on for other positions.

Figure 12:
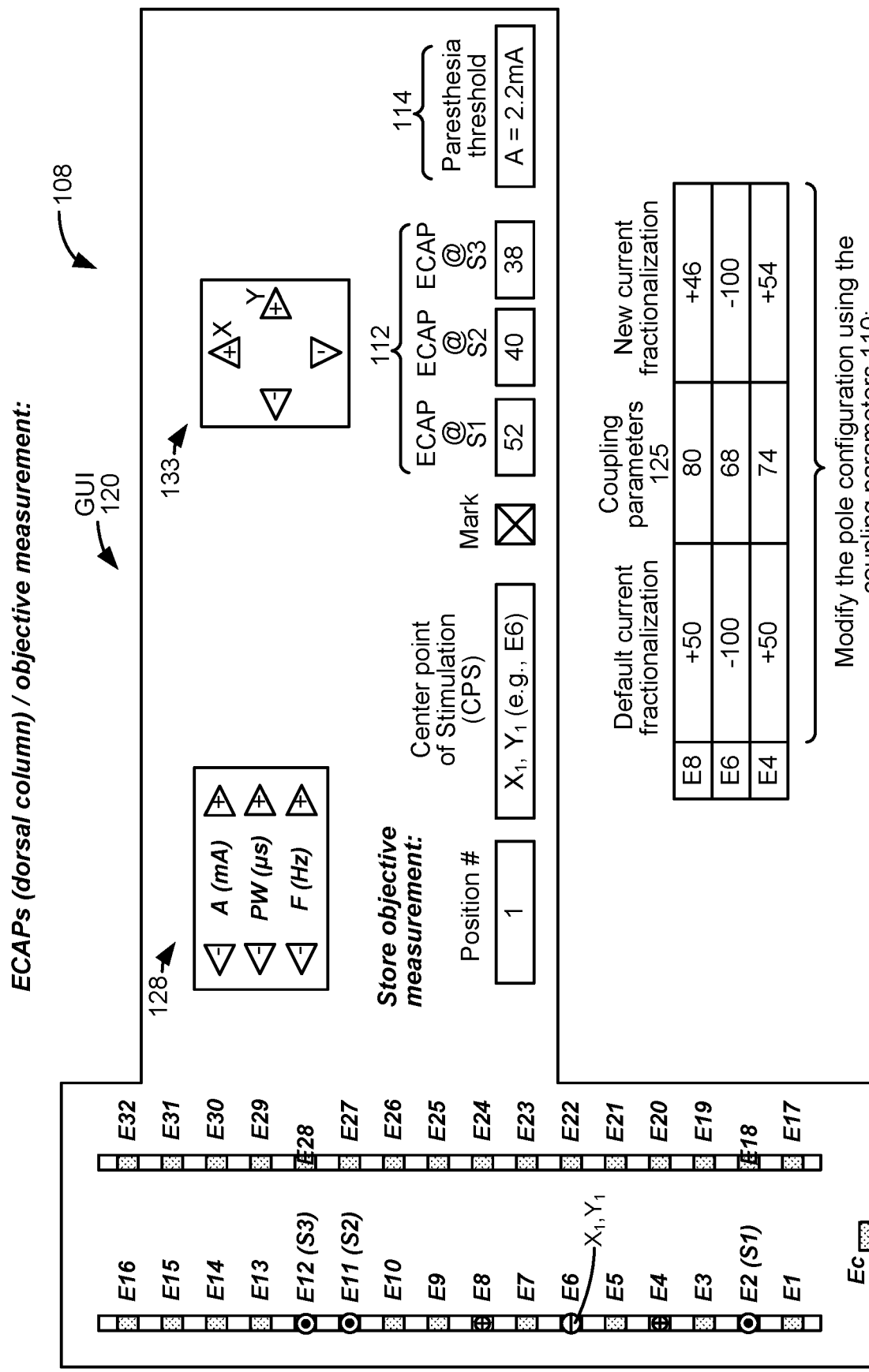
FIG. 12 shows an example in which a tripole configuration designed to recruit neural targets in the dorsal column is steered to different position in the electrode array, and shows recording of different objective measurements of effectiveness at each position, as well as a paresthesia threshold at each position.

FIG. 12 shows another example pole configuration steering 108, which again assumes that the clinician has earlier selected from table 131 (FIG. 9) to use a tripole during steering to recruit the dorsal column as an anatomical target. Further, it is assumed in the example that the clinician has selected row 2 in the table 131, and therefore that objective measurements (M) will be taken from the patient during steering. Specifically, the measurements comprise monitoring an ECAP feature, such as amplitude, although again other objective measures could be assessed.

This fitting algorithm 100 process is otherwise similar. The pole configuration can be modified using the stored coupling parameters (110). In this example, ECAP amplitudes (FIG. 8B) are used as the coupling parameters CP for each electrode, but subjectively-determined coupling parameters could also have been used (FIG. 8A) to modify the pole configuration. One or more objective measurements are taken (112), and as prescribed by table 131, such measurements are taken at one or more of electrodes E2 (S1), E11 (S2), and E12 (S3), which will vary based on the current position of the tripole. Selecting to mark this position can inform the clinician programmer 70 to wirelessly instruct the IPG 10 or ETS 50 to take the necessary measurements at the necessary electrodes, and to wirelessly transmit the measurements back to the clinician programmer 70 for storage. Alternatively, the IPG 10 or ETS 50 can provide the clinician programmer 70 data indicative of the measurement (e.g., the sampled waveform of the ECAPs), with the clinician programmer then analyzing the data to extract the measurement (the ECAP amplitude). Again, the paresthesia threshold PT of the tripole is taken by adjusting the amplitude A (114) to a lowest level at which the patient can feel stimulation as provided by the pole configuration. After recording such measurement(s) and the paresthesia threshold at the first position, the pole configuration can then steered to a new location (133) and the process repeated.

Figure 13A:
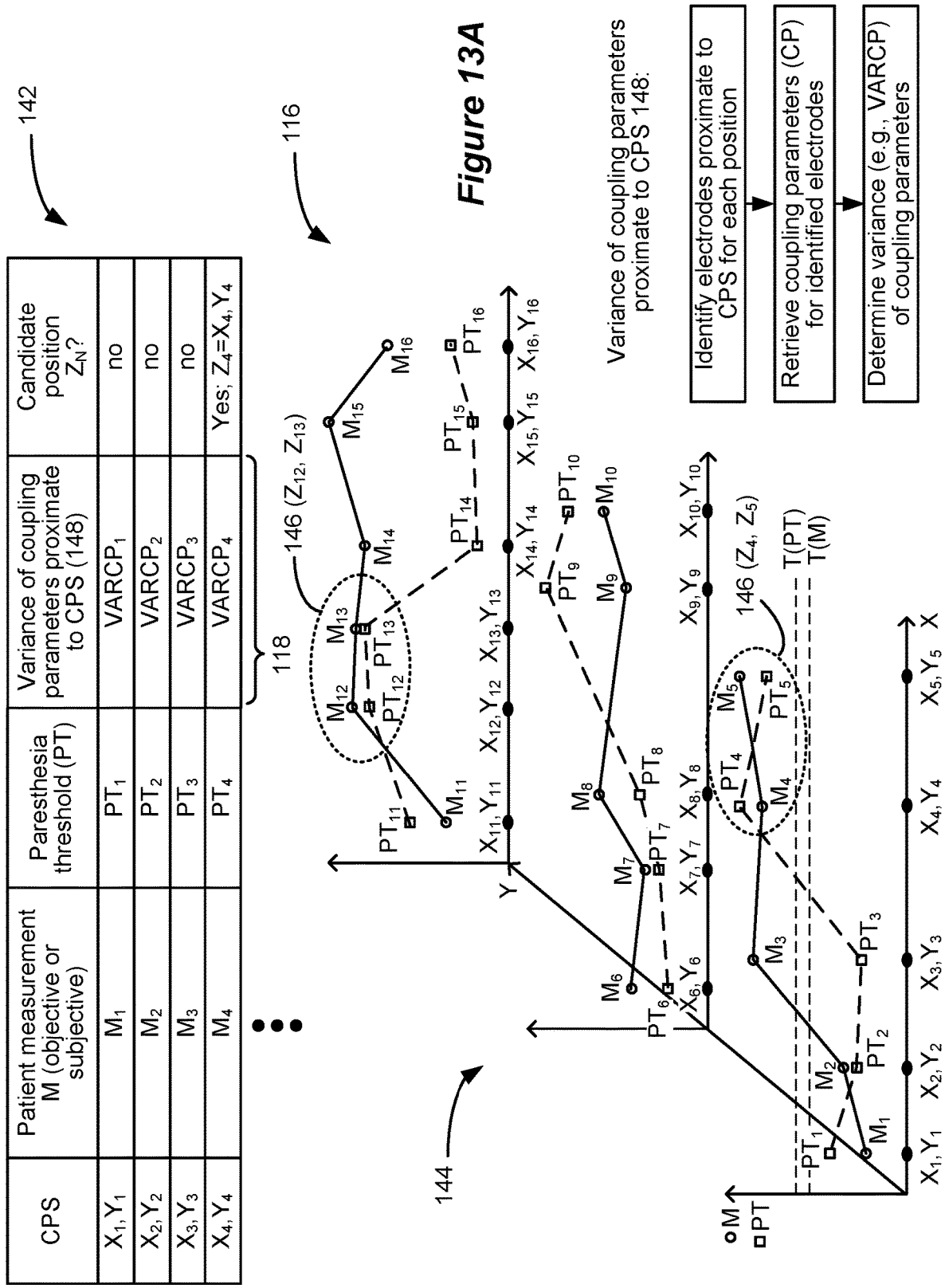
FIGS. 13A and 13B shows different manners of evaluating of the stored measurements at each position to determine one or more candidate positions for the application of therapeutic stimulation programs.

After the pole configuration has been steered and measurements taken, fitting algorithm 100 can proceed to evaluate the stored data at each position to select one or more candidate positions $Z_N$ at which eventual therapy can be applied (116, FIG. 6). An example of this evaluation step 116 is shown in FIG. 13A. A table 142 shows relevant data taken and stored in the clinician programmer 70 at each pole configuration position ($X_N, Y_N$) during steering, including the one or more measurements ($M_N$) taken at that position and the paresthesia threshold ($PT_N$) of the pole configuration at that position. This data is graphed 144 in FIG. 13A in two dimensions X and Y covering the span of the electrode array 17 or 17'. Graphing eases understanding of the evaluation of the results, and graph 144 may be displayed in GUI 120, although this isn't strictly necessary. In this example, it is assumed that higher values for M correspond to better patient results, but this isn't strictly necessary, because, depending on the nature of the measurement, lower values for M may indicate better patient results.

It is also assumed that higher values for the paresthesia threshold PT of the pole configurations are a preferred result, but again this depends on the manner in which the paresthesia threshold is quantified. In this example, when the paresthesia threshold comprises a lowest current felt by the patient, a higher value is deemed better. This is because an eventual therapy stimulation program, if placed at this position, should have more headroom or range for current adjustment and be less sensitive to changes such as electrode movement due to postural changes, migration of the electrodes in the spinal column over time, scar tissue formation, etc. If the paresthesia threshold PT is lower, there is less room for current adjustment, especially if sub-perception therapy is to be used. Further, a lower paresthesia threshold PT runs a greater risk of subjecting the patient to excessive therapeutic currents if changes occur. This can be a concern for example if the patient's posture changes in a manner that brings the electrode array closer to relevant neural structures. If the paresthesia threshold is low, the prescribed therapeutic current may suddenly be too high for the patient, which may be uncomfortable. Stated simply, a position with a higher paresthesia threshold PT allows for more freedom is choosing therapeutic currents, and is less sensitive to postural changes and other patient and/or electrode movements.

Accordingly, in this example and in graph 144, possible candidate positions $Z_N$ for therapy correspond to positions 146 where both the measurements M and the paresthesia thresholds PT are both high, which include positions $X_4,X_4$ ($Z_4$), $X_5,Y_5$ ($Z_5$), $X_{12},Y_{12}$ ($Z_{12}$), and $X_{13},Y_{13}$ ($Z_{13}$). In this regard, thresholds T(M) and T(PT) can be used to determine whether the measurement M and paresthesia threshold PT are suitable for use as a candidate position $Z_N$, and it can be see that both exceed these thresholds at $Z_4$, $Z_5$, $Z_{12}$, and $Z_{13}$. Determination of candidate positions $Z_N$ preferably occur automatically in the fitting algorithm 100 with reference to thresholds or in accordance with other computational techniques described subsequently.

Determining candidate positions $Z_N$ for therapy can involve the consideration of other factors as well. For example, and as shown in Table 142, the variance of the coupling parameters CP proximate to the electrodes used to create the pole configurations at each position, or more simply just the electrodes used to create the pole configurations at each position, can be assessed (see 118, FIG. 9). By way of review, these coupling parameters were determined earlier in steps 102 and 104 and stored in database 125 (see FIGS. 8A and 8B). Generally speaking, it is preferred that variance of the electrode coupling parameters near a candidate position be low. This is because as mentioned earlier the electrode array 17 or 17' can migrate in a patient over time or as the patient moves. Low variance also implies a "uniform" spinal cord physiology (e.g., no unusual tissue features, scarring, dimples or ridges in the CSF thickness, etc.) proximate to the position. If the variance is high, the therapy stimulation program might be more sensitive, and require more frequent adjustment.

One example of determining coupling parameter variance and implementable in the clinician programmer 70 as an algorithm 148 is shown at the bottom of FIG. 13A. The variance algorithm 148 can determine which electrodes are generally proximate to the central point of stimulation (CPS) of the pole position at a given measured position. The may include all electrodes that are a certain distance from the CPS, or perhaps just the electrodes used to produce the pole configuration. The coupling parameters CP for those electrodes are retrieved, i.e., from database 125 (FIGS. 8A and 8B). Then, a measure of variance is determined for the retrieved coupling parameters. In a simple example, this can comprise computing a standard deviation of the coupling parameters, although other statistical means can be used to determine variance. In another example, the variance may simply comprise the spread or range of the retrieved coupling parameter values. Once the variance of the coupling parameters is determined at each of the positions (VARCP), this variance can be included and stored in table 142 are shown. Although this variance VARCP is not graphed in FIG. 13A, it could be, and further a threshold (T(VARCP)) could be established, with variances below this threshold being deemed suitable in the identification of candidate positions $Z_N$.

Figure 13B:
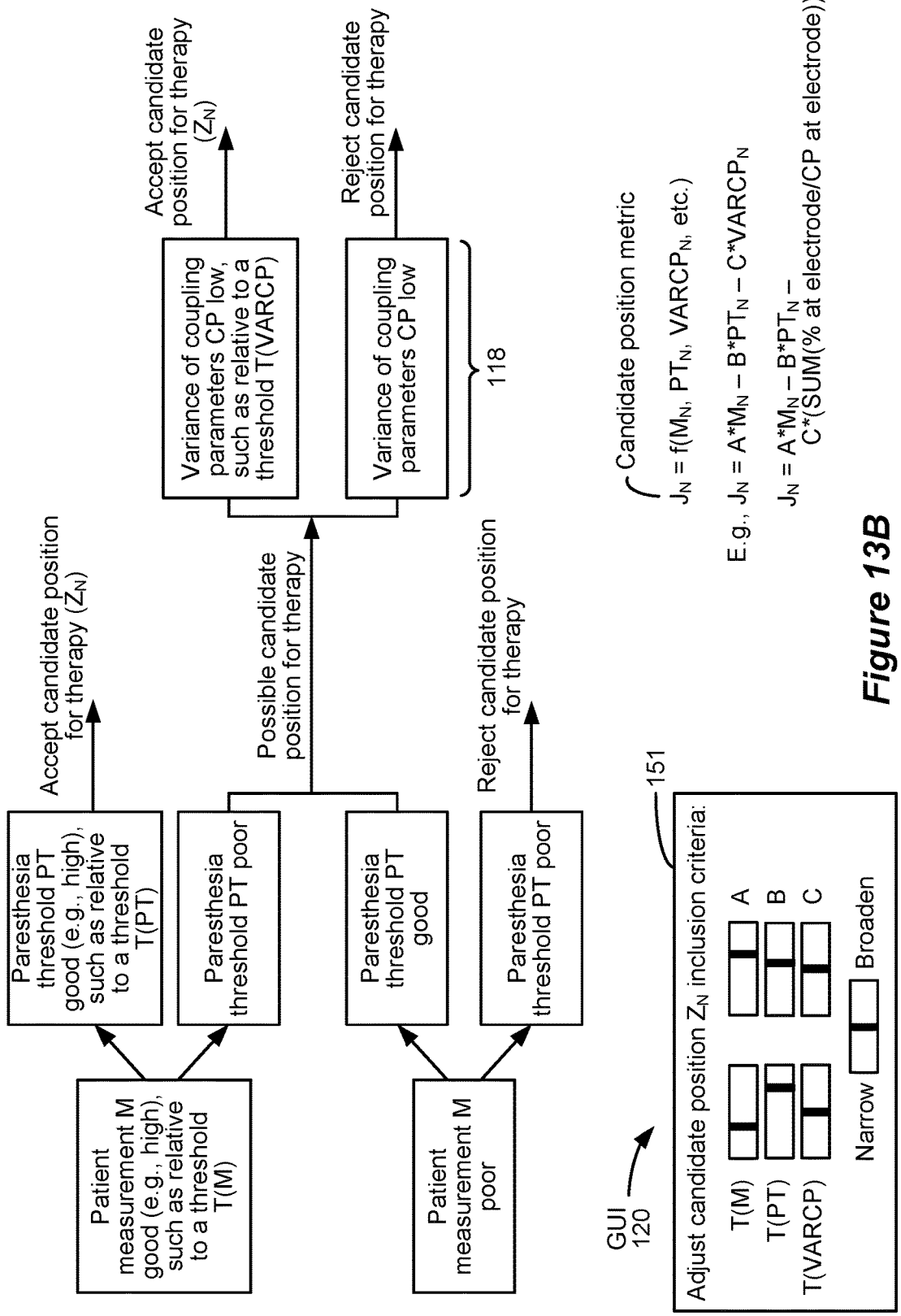

FIG. 13B shows another algorithm that the clinician program can use at step 116 to identify candidate positions $Z_N$ for the later application of therapeutic stimulation programs. In this example, the algorithm comprises a flow chart which can be run on each position (e.g., each row in table 142). As a first step, the algorithm determines if a position has a good (e.g., high) or poor (e.g., low) patient measurement M, which can be assessed using the measurement threshold T(M) discussed earlier. The algorithm then looks at the paresthesia threshold PT at this position to determine if it is good (e.g., high) or poor (low), which can be assessed using threshold T(PT) discussed earlier. If both the measurement M and paresthesia threshold PT are good, that position is accepted as a candidate position $Z_N$ for the application of a therapeutic stimulation program. If both the measurement M and paresthesia threshold PT are poor, that position is rejected as a candidate position.

If one of the measurement M or paresthesia threshold PT is good but the other is poor, the positions may possibly be candidate position, and the algorithm may investigate further by optionally reviewing (step 118, FIG. 6) the variance of the coupling parameters, VARCP, as discussed with respect to FIG. 13A. If the variance is low, such as determined with reference to a variance threshold T(VARCP), the possible candidate position is accepted as a candidate position ZN; if high, the possible candidate position is rejected.

Determination of candidate positions $Z_N$ can occur in other ways. For example, and as shown in FIG. 13B, one or more equations can be used to determine a candidate position metric $J_N$. Generally speaking, whether a pole configuration position can act as a candidate position $Z_N$ depends on the measurement $M_N$, the paresthesia threshold $PT_N$, and optionally the coupling parameter variance $VARCP_N$ taken at each pole configuration position $X_N,Y_N$, and these values can be processed in various ways to compute a candidate position metric $J_N$ for each position. For example, $M_N$, $PT_N$ and $VARCP_N$ can be multiplied by weighting factors A, B and C respectively, and then added or subtracted to compute the candidate position metric $J_N$ at each position. In another example shown, the current fraction percentage at each of the electrodes used to create the pole configuration can be divided by its coupling parameter, with these ratios summed and multiplied by a weighting factor C if necessary. In any event, by processing the values from table 146, a candidate position metric $J_N$ can be calculated indicative of the goodness or the poorness of the pole configuration at that position. The best candidate position metrics $J_N$ (e.g., the three highest or lowest, depending on the manner in which the metric is calculated) or those above or below a $J_N$ threshold might for example be considered as candidate solutions Zn.

The GUI 120 may contain aspects to allow the clinician to control the candidate position determination to some degree, and a candidate position interface 151 is shown in FIG. 13B. Generally speaking, the candidate position interface 151 allows various factors useable to determine candidate positions $Z_N$ to be adjusted, and so can affect the number of candidate positions that the algorithm might suggest. For example, sliders can be used to adjust the measurement threshold T(M) and the paresthesia threshold T(PT) to higher or lower values. If higher measurements M and paresthesia threshold PT are beneficial to the patient, increasing either or both of these thresholds will reduce the number of possible candidate solutions $Z_N$ that the algorithm 116 determines, while decreasing either or both will increase the number of possible candidate solutions that the algorithm 116 determines. A slider may also be used to adjust the coupling parameter variance threshold T(VARCP), which would alter the determination of candidate positions in the flow chart of FIG. 13B (118). Sliders may also be used to adjust the weights A, B, and C that might be used in the computation of a candidate position metric $J_N$, which again could change the suggest candidate positions $Z_N$. Finally, a generic slider can be used to broaden or narrow the number of candidate positions $Z_N$ output by the algorithm, which may change one or more of the thresholds or weights just discussed.

Figure 14:
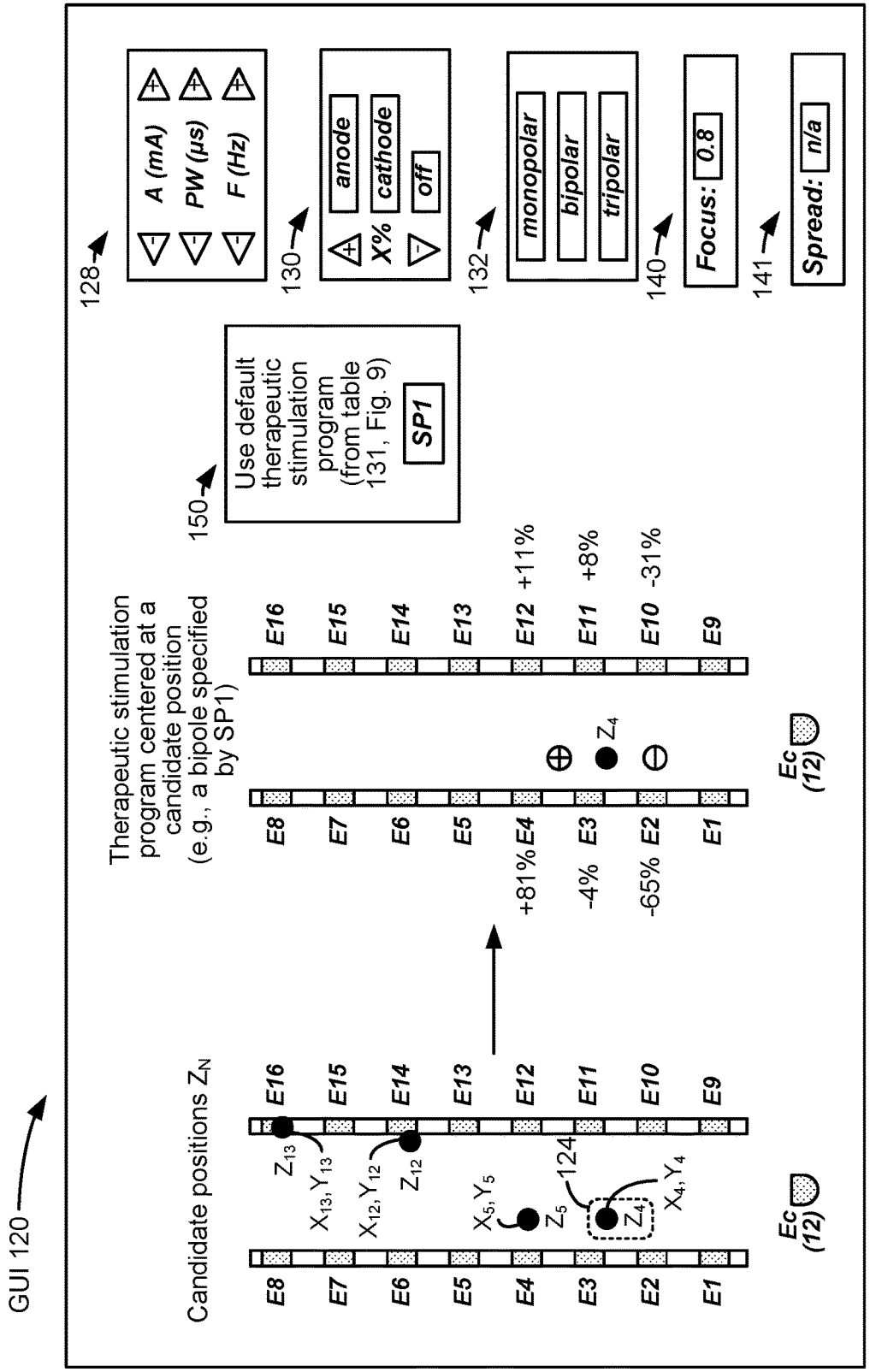
FIG. 14 shows application of a therapeutic stimulation program at one or more of the determined candidate positions.

Once one or more candidate positions $Z_N$ have been chosen, fitting algorithm 100 can proceed to step 119 (FIG. 6), where a therapeutic stimulation program can be chosen for the patient that is centered at one of the candidate positions. FIG. 14 shows an example of the GUI 120 at this step 119. As shown to the left, the candidate positions $Z_N$ determined earlier as being successful positions at which to try therapeutic stimulation programs can be shown overlaid on the electrode array 17 or 17', and in this example it is assumed that four candidate positions $Z_4$ ($X_4,X_4$), $Z_5$ ($X_5$, $Y_5$), $Z_{12}$ ($X_{12},Y_{12}$), and $Z_{13}$ ($X_{13},Y_{13}$) have been determined.

The clinician may now select any of these candidate positions (e.g., $Z_4$) using cursor 124 for example, and devise a therapeutic stimulation program that is centered at that position. The clinician could do this manually. For example, the clinician could select for example to try a bipole (132) centered at this position as shown. Notice that the anode (+) and cathode (−) poles of the bipole are equally spaced from, and thus center, candidate position $Z_4$. Once this bipole has been positioned, it can thereafter be modified as necessary to create the therapeutic stimulation program. For example, the positions of the poles can be varied with respect to the center $Z_4$, such as by using the focus interface 140. Further adjustments to arrive at the therapeutic stimulation program can include varying the parameters in parameter interface 128 (A, PW, f). Note that the therapeutic stimulation program eventually used for the patient's therapy need not be different from the pole configuration used during sweet spot searching (108, FIG. 6). For example, if a spread monopole was used during sweet spot searching, it could again be used as the therapeutic stimulation programs.

Note that the clinician may wish to try therapeutic stimulation programs at one, more, or all of the candidate solutions, to try and determine one or more therapeutic stimulation programs that work best for the patient. Still, while some degree of experimentation may be warranted at step 119 to determine one or more therapeutic stimulation programs, use of the fitting algorithm 100 greatly assists the clinician and conveniences the patient, because the candidate solutions narrow the possible positions at which therapeutic stimulation should be placed.

Interface 150 may also allow the clinician to choose a default therapeutic stimulation program (SP1) centered at one of the candidate positions $Z_N$. This default therapeutic stimulation program may comprise one associated with the steering pole configuration, anatomical target, and measurement technique that was selected earlier (table 131, FIG. 9). For example, if row 1 was selected in table 131, a default stimulation program SP1 may be populated in interface 150. Alternatively, and although not shown, each row in table 131 may be associated with a number of default therapeutic stimulation programs, each of which can then be populated in interface 150 for selection by the clinician. Although not shown, interface 150 may include certain information about the one of more default therapeutic stimulation programs, such as their basic parameters (e.g., A, PW, f), its pole configuration or other details or descriptors of clinician significance.

Certain default therapeutic stimulation programs associated in table 131 can be logically structured in light of the anatomical targets deemed to be of interest during sweet spot searching. For example, if the dorsal column was the target of interest during sweet spot searching based on a patient's symptoms, it may also be of interest when the therapeutic stimulation programs is used, even if a different pole configuration is used. For example, and as shown in FIG. 15, a more-focused bipole configuration may be used for therapy, even though a tripole configuration was used during sweet spot searching. It may be ideal in this circumstance that the therapeutic stimulation program be sub-perception, even though paresthesia was used during the sweet spot search. In this case, the default therapeutic stimulation program may have a low amplitude A, or may have a high frequency (e.g., >1 kHz), because there is some evidence to suggest that high frequency stimulation is useful to providing sub-perception therapy. In another example, while it was useful to target a particular anatomical target during sweet spot searching, the default stimulation program may be designed to target a different anatomical target.

While it is preferred that the therapeutic stimulation program be centered at the candidate positions, it should be understood that such centering may not be exactly perfect. System limitations may prevent such perfect centering. For example, while an electrode configuration algorithm can be used to activate certain electrodes to approximate the desired positions of poles in an electrode array, such approximations are not perfect. As a result, the central point of stimulation of a steering pole configuration determined as a candidate position may not exactly match the central point of stimulation of a pole configuration used in a therapeutic stimulation program. It should therefore be understood in context that determined candidate positions and the central point of stimulation of therapeutic stimulation programs can be said to be "centered" if they vary by 3 mm or less.

While disclosed in the context of a spinal cord stimulation system, it should be understood that the disclosed fitting algorithm can be employed in other neurostimulation systems. As used herein, the "spinal cord" should be understood as comprising all the neural structures within the gray and white matter of the spinal column as well as neural structures that branch into or out of the spinal cord, such as the dorsal and ventral columns, the dorsal and ventral horns, the dorsal and ventral roots, the dorsal root ganglion, other spinal nerves, etc.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for configuring an implantable stimulator device for a patient using an external system in communication with the implantable stimulator device, wherein the implantable stimulator device comprises an electrode array implanted in the patient, the method comprising:
    (a) providing a plurality of selectable options in a user interface of the external system, wherein each selectable option comprises an anatomical target, wherein each anatomical target is associated in the external system with a pole configuration configured to recruit that anatomical target;
    (b) receiving an input at the user interface to select one of the anatomical targets; and (c) applying the pole configuration associated with the selected anatomical target at a position in the electrode array.

2. The method of claim 1, wherein each pole configurations comprise a position of one or more poles and a current fraction for each one or more poles.

3. The method of claim 1, wherein the pole configurations associated with the anatomical targets are different for at least some of the anatomical targets.

4. The method of claim 1, wherein the pole configurations associated with the anatomical targets are different for all of the anatomical targets.

5. The method of claim 1, wherein the electrode array is implanted in a spinal column of the patient, wherein each anatomical target comprises a different structure in a spinal cord of the patient.

6. The method of claim 1, wherein each selectable option is further associated in the external system with a measurement, wherein each measurement is configured to gauge the effectiveness of its associated pole configuration.

7. The method of claim 6, wherein the measurements associated with the anatomical targets are different for at least some of the anatomical targets.

8. The method of claim 6, wherein at least one of the measurements comprises a subjective measurement comprising patient feedback.

9. The method of claim 8, wherein the subjective measurement comprises patient feedback concerning how effectively the searching pole configuration addresses a symptom of the patient or produces sequelae at a dermatomal or anatomical location in the patient.

10. The method of claim 6, wherein at least one of the measurements comprises an objective measurement taken from the patient.

11. The method of claim 10, wherein the objective measurement is taken by the implantable stimulator device.

12. The method of claim 1, wherein the user interface of the external system displays each selectable option including its anatomical target and its associated pole configuration.

13. The method of claim 1, further comprising (d) receiving inputs at the user interface to move the pole configuration associated with the selected anatomical target to different positions in the electrode array.

14. The method of claim 1, wherein each selectable option is further associated in the external system with a stimulation program.

15. The method of claim 14, wherein the pole configuration is applied at the position in the electrode array in accordance with the stimulation program associated with the selected anatomical target.

16. The method of claim 1, further comprising, in step (c), determining a paresthesia threshold for the applied pole configuration, and storing the paresthesia threshold in a memory in the external device.

17. A system, comprising:
   an implantable stimulator device, wherein the implantable stimulator device comprises an electrode array implantable in the patient; and
   an external system, comprising:
      a user interface configured to provide a plurality of selectable options, wherein each selectable option comprises an anatomical target, wherein each anatomical target is associated in the external system with a pole configuration configured to recruit that anatomical target,
      wherein the user interface is configured to receive an input at the user interface to select one of the anatomical targets, and
      wherein the external system is configured to apply the pole configuration associated with the selected anatomical target at a position in the electrode array.

18. The system of claim 17, wherein each pole configurations comprise a position of one or more poles and a current fraction for each one or more poles.

19. The system of claim 17, wherein the pole configurations associated with the anatomical targets are different for at least some of the anatomical targets.

20. A system, comprising:
   an implantable stimulator device, wherein the implantable stimulator device comprises an electrode array implantable in the patient; and
   a non-transitory computer readable comprising instructions, wherein the instructions are configured to be executed on an external system in communication with the implantable stimulator device, wherein the instructions when executed are configured to:
      (a) provide a plurality of selectable options in a user interface of the external system, wherein each selectable option comprises an anatomical target, wherein each anatomical target is associated in the external system with a pole configuration configured to recruit that anatomical target;
      (b) receive an input at the user interface to select one of the anatomical targets; and
      (c) apply the pole configuration associated with the selected anatomical target at a position in the electrode array.

* * * * *